United States Patent
Dimitroff

(10) Patent No.: US 11,976,118 B2
(45) Date of Patent: May 7, 2024

(54) THERAPIES FOR B CELL MALIGNANCIES

(71) Applicant: Charles J. Dimitroff, Coral Gables, FL (US)

(72) Inventor: Charles J. Dimitroff, Coral Gables, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 33 days.

(21) Appl. No.: 17/371,770

(22) Filed: Jul. 9, 2021

(65) Prior Publication Data
US 2023/0009888 A1    Jan. 12, 2023

(51) Int. Cl.
*C07K 16/28* (2006.01)
*A61K 38/17* (2006.01)
*A61K 39/00* (2006.01)
*A61P 35/00* (2006.01)

(52) U.S. Cl.
CPC ...... *C07K 16/2803* (2013.01); *A61K 38/1732* (2013.01); *A61P 35/00* (2018.01); *A61K 2039/505* (2013.01)

(58) Field of Classification Search
None
See application file for complete search history.

(56) References Cited

U.S. PATENT DOCUMENTS

2015/0216931 A1*  8/2015  Chiriva-Internati ........................ C07K 14/4726
                                                                    514/19.5
2016/0264670 A1*  9/2016  Graziano ........... C07K 16/2806

OTHER PUBLICATIONS

EMPLICITI® (Prescribing Information, Mar. 2022) (Year: 2022).*
Kobayashi et al. (Leukemia 2010 24: 843-850), (Year: 2010).*
Mirandola et al. (International Rev. Immunology 2014 33: 417-427) (Year: 2014).*
Chakraborty, A., et al. "Galectin-9 bridges human B cells to vascular endothelium while programming regulatory pathways." Journal of Autoimmunity 117 (2021): 102575. pp. 1-13.

* cited by examiner

*Primary Examiner* — Peter J Reddig
(74) *Attorney, Agent, or Firm* — SALIWANCHIK, LLOYD & EISENSCHENK

(57) ABSTRACT

The subject invention provides novel methods for treating B cell malignancies, such as multiple myeloma, using a combination therapy. Said treatment in accordance with the subject invention comprises the administration of a B cell regulator, e.g., a galectin molecule, to a subject suffering from a B cell malignancy, and wherein said subject received, receives, or will receive a treatment with a conventional treatment for such B cell malignancy, e.g., immunotherapy. The administration of the galectin molecule boosts the expression of B cell specific antigens e.g., SLAMF7, on MM cells, thereby increasing the sensitivity of MM cells to anti-SLAMF7 Ab and therapeutic efficacy of Elotuzumab.

19 Claims, 12 Drawing Sheets
(8 of 12 Drawing Sheet(s) Filed in Color)

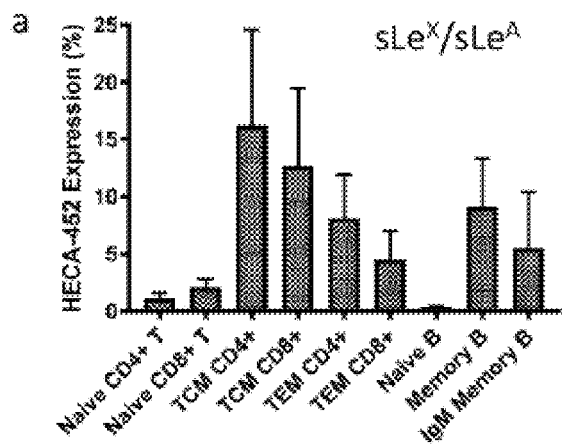
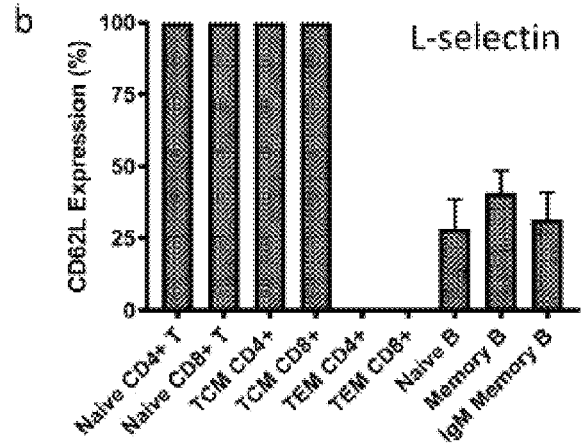
FIG. 2A
FIG. 2B
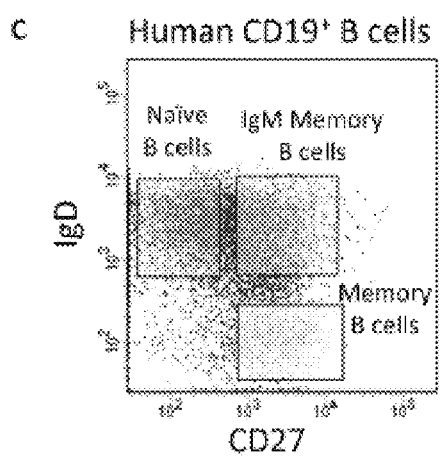
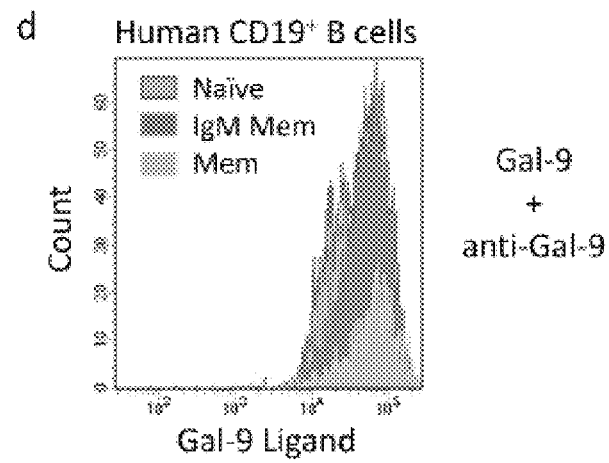
FIG. 2C
FIG. 2D

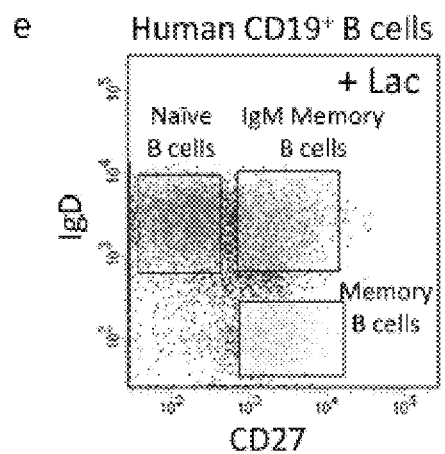
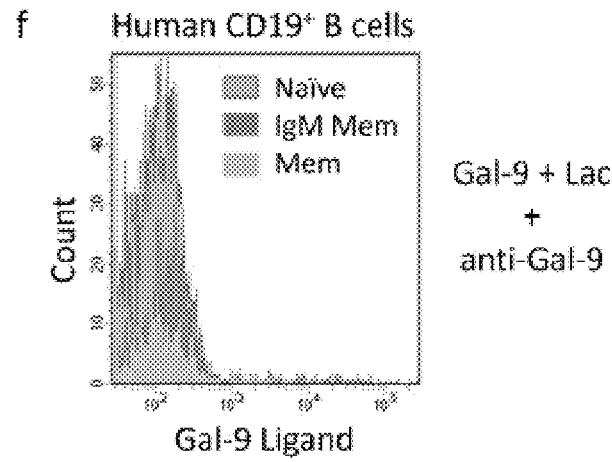
FIG. 2E
FIG. 2F
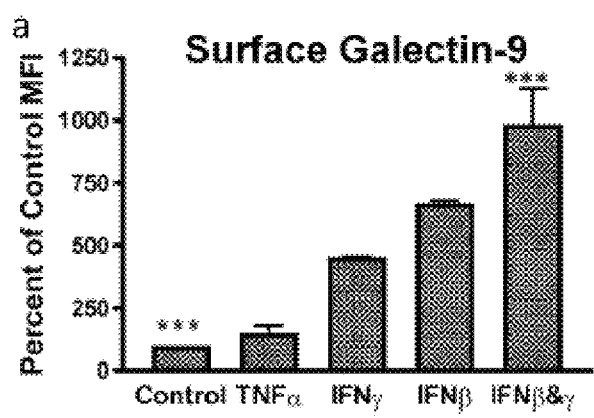
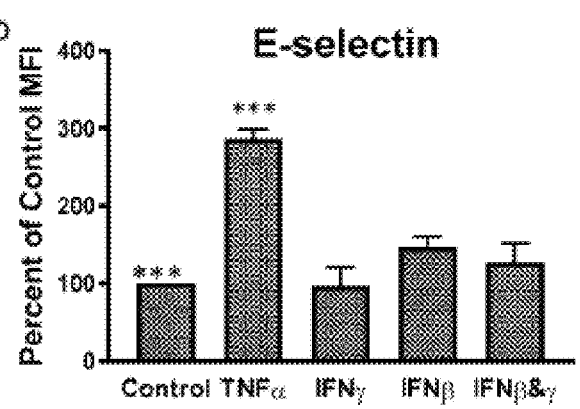
FIG. 3A
FIG. 3B

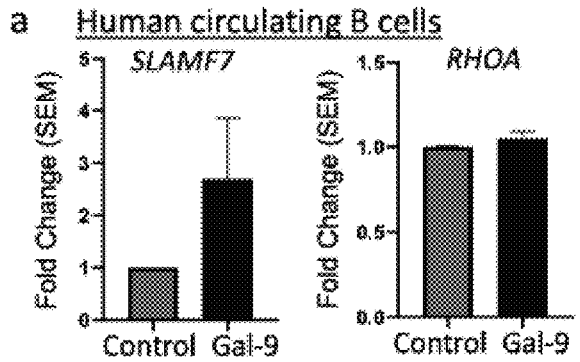
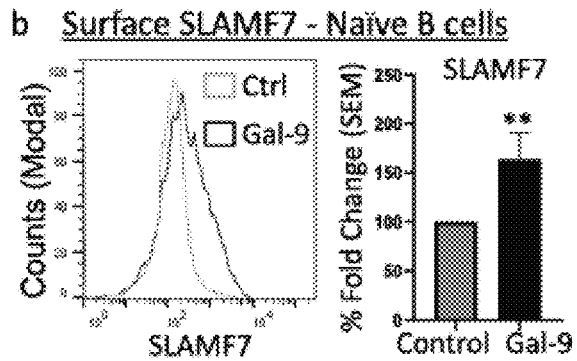
FIG. 6A  FIG. 6B
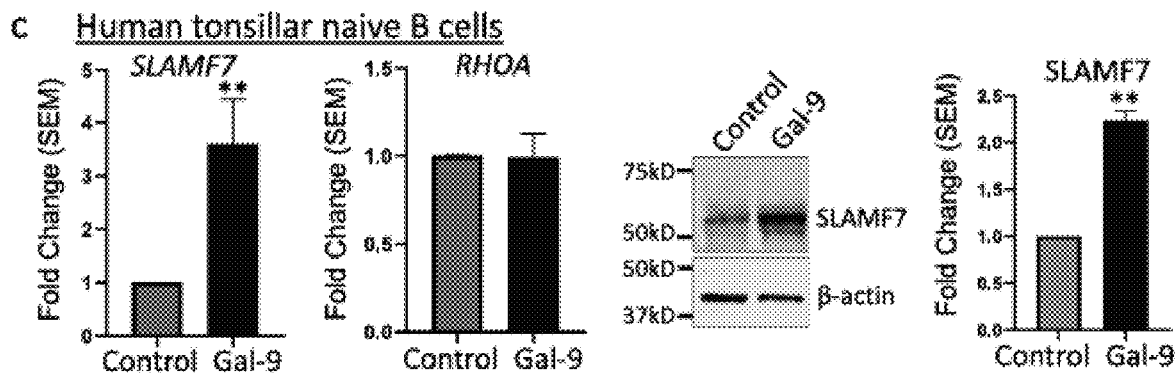
FIG. 6C
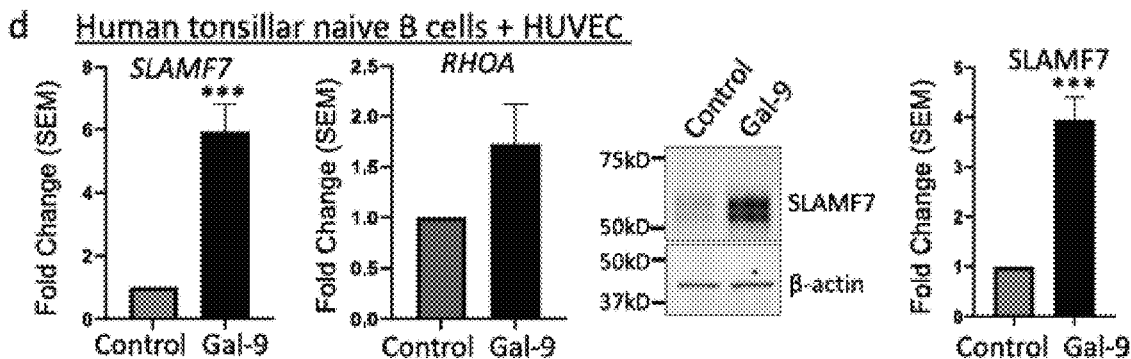
FIG. 6D

THERAPIES FOR B CELL MALIGNANCIES

GOVERNMENT SUPPORT

This invention was made with government support under AI146368 awarded by the National Institutes of Health. The government has certain rights in the invention.

BACKGROUND OF THE INVENTION

Strategies to boost antibody (Ab) B cell responses to vaccines or blunt Ab production associated with autoimmune disorders are under intense investigation. However, the molecular factors driving effective functional transition from naïve B cells to germinal center (GC) B cells, memory B cells and Ab-producing plasma cells are still poorly defined.

Galectins are a family of 15 evolutionarily conserved glycan-binding proteins (lectins) widely expressed in both stromal and immune tissues. Extensive research has established galectins as important regulators of immune homeostasis, inflammation, malignancy, and autoimmune disease. In innate immunity, galectins are known to regulate granulocyte chemotaxis, dendritic cell maturation, mast cell activation, and many other activities. In adaptive immunity, galectins are perhaps most widely recognized for their effects on T cell function, where galectins (Gal)-1, -3, and -9 have been shown to differentially modulate development, activation, differentiation, and effector function. While significant progress has been made in deciphering roles of galectins in innate immune cell and T cell biology, the roles for galectins in B cells are not fully understood.

Gal-9 is emerging as a key regulator of BCR signaling and activation. Early studies in mice lacking Gal-9, in fact, reveal increased viral-specific IgM, IgG and IgA titers and enhanced formation of Ab-secreting cells in response to influenza A challenge. These studies demonstrate that rGal-9 or mesenchymal stem cell-derived Gal-9 antagonize human B cell proliferation and Ab-secreting cell formation, and mice treated with rGal-9 result in diminished Ag-specific serum titers in response to immunization and suppressed a mouse model of lupus. Gal-9 effects on both human and mouse naïve B cells negatively regulate BCR signaling.

Cell surface glycans are increasingly recognized for their key regulatory functions during immune homeostasis and inflammation by providing binding moieties for native glycan-binding lectins that can impact leukocyte homing, adhesion, pathogen sensing and signaling. In B cells, sialoglycans, which bind CD22/Siglec-2 and Siglec-G, help regulate B cell receptor (BCR) signaling and peripheral tolerance. B cell sialylation, importantly, represents only a small fraction of the glycans on B cells. Germinal center (GC) B cells, as an example, express glycan features, including T-antigen, loss of GlcNAc sulfation, CD77/Gb3 glycolipid and GL7/α2,6-sialyl-LacNAc, though their functions remain enigmatic.

The N-glycome is characterized by an abundance of linear poly-N-acetyllactosamines (poly-LacNAc) on naïve/memory B cells and "I"-branched poly-LacNAcs on GC B cells. Poly-LacNAcs are canonical glycans for binding galectins and decorate a variety of cell surface receptors that can transmit regulatory signals to a cell. In particular, Gal-9, best known for its inhibitory role on inflammatory T cell responses, avidly binds poly-LacNAcs. Human naïve/memory B cells express mainly linear poly-LacNAcs and strongly bind Gal-9, whereas GC B cells express GCNT2-synthesized I-branched poly-LacNAcs and poorly bind Gal-9. Gal-9-binding to naive B cells induces Lyn-CD22-SHP-1 signaling and suppresses BCR-mediated Ca++ flux, NFAT1 nuclear translocation and activation/proliferation.

The plasma cell malignancy, known as Multiple Myeloma (MM), is a lethal disease resulting in a 5-year survival rate of only 50%. MM is an incurable disease with a high rate of recurrence and there is, thus, critical need for new therapies. Current treatments, such as proteasome inhibitors and immunomodulatory drugs, have significantly increased the remission rate, however, more recent immunotherapeutic strategies have emerged as promising therapies for MM disease.

Effective development of antibody (Ab) immune responses is dependent on the localization of naïve B cells into secondary lymphoid organs and, upon antigen activation, their coordinated differentiation into Ab-producing plasma cells. Thus, there is a need to expand mechanistic knowledge of these factors controlling B cell differentiation, and develop therapeutic methods for boosting Ab-production in vaccines, blunting Ab-production in autoimmunity and/or restricting the progression of B cell malignancies.

BRIEF SUMMARY OF THE INVENTION

The subject invention provides novel strategies, methods, and compositions for treating B cell malignancies and restricting the progression of B cell malignancies, in particular, B cell derived cancers, for example, multiple myeloma (MM).

In one embodiment, the subject invention provides a method for treating a B cell malignancy using a combination therapy. In one embodiment, the treatment in accordance with the subject invention comprises the administration of a B cell regulator, e.g., a galectin molecule, to a subject suffering from a B cell malignancy, and wherein the subject received, receives or will receive a treatment with a conventional treatment for such B cell malignancy, e.g., immunotherapy.

In one embodiment, the subject invention provides a method for treating a B cell malignancy in a subject in need of such treatment, comprising administering to the subject a composition comprising a galectin molecule; and administering to the subject a composition comprising an antibody that specifically binds to a B cell specific antigen, wherein each administration is independently selected from, for example, local, oral, nasal, topical, intratumoural, transdermal, intra-articular, intravenous, intraperitoneal, intradermal, subcutaneous, and intramuscular routes.

In a specific embodiment, the galectin molecule is a galectin protein or a nucleotide sequence encoding the galectin protein. In a preferred embodiment, the galectin molecule is galectin-9 protein or a nucleotide sequence encoding the galectin-9 protein.

In specific embodiments, the B cell specific antigen is selected from SLAMF7, FCRL4, CCL22, DUSP8, CCL4, SIGLEC10, FCER2, ZEB1, PPP1R26, GAB2 and DOK37. Preferably, the B cell specific antigen is SLAMF7.

In a specific embodiment, the antibody is an antibody that specifically binds to SLAMF7, e.g., Elotuzumab.

In one embodiment, the invention provides a method for treating multiple myeloma in a subject, comprising:
   administering to the subject a composition comprising 1) a nucleic acid sequence that encodes Gal-9 or a nucleic acid sequence that encodes a protein sharing at least 95% identity with Gal-9, 2) an amino acid sequence of Gal-9 or an amino acid sequence sharing at least 95% identity with Gal-9, 3) a vector comprising a nucleic acid sequence that encodes Gal-9 or a nucleic acid sequence that encodes a protein sharing at least 95% identity with Gal-9, 4) a cell that overexpresses a nucleic acid sequence of Gal-9 or a nucleic acid sequence that encodes a protein sharing at least 95% identity with Gal-9, and/or 5) a cell that overexpresses an amino acid sequence of Gal-9, or an amino acid sequence sharing at least 95% identity with Gal-9; and administering to the subject a composition comprising an antibody that specifically binds to a B cell specific antigen.

In specific embodiments, each administration is independently selected from local, oral, nasal, topical, intratumoural, transdermal, intra-articular, intravenous, intraperitoneal, intradermal, subcutaneous, and intramuscular routes.

In one embodiment, the subject invention provides a method for improving the sensitivity of multiple myeloma cells of a subject to an immunotherapy, the method comprising administering to the subject a composition comprising 1) a nucleic acid sequence that encodes Gal-9 or a nucleic acid sequence that encodes a protein sharing at least 95% identity with Gal-9, 2) an amino acid sequence of Gal-9 or an amino acid sequence sharing at least 95% identity with Gal-9, 3) a vector comprising a nucleic acid sequence that encodes Gal-9 or a nucleic acid sequence that encodes a protein sharing at least 95% identity with Gal-9, 4) a cell that overexpresses a nucleic acid sequence of Gal-9 or a nucleic acid sequence that encodes a protein sharing at least 95% identity with Gal-9, and/or 5) a cell that overexpresses an amino acid sequence of Gal-9, or an amino acid sequence sharing at least 95% identity with Gal-9; and administering to the subject the immunotherapy.

In a preferred embodiment, the immunotherapy is an antibody therapy comprising administering to the subject an anti-SLAMF7 antibody, e.g., Elotuzumab.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2A-2F show that human circulating B cells express low levels of sialyl LewisX/A and L-selectin and high levels of Gal-9 ligand. PBMC were stained with antibodies to T cell markers (CD3, CD4 and CD45RO) or to B cell markers (CD19, IgD, CD27) and either anti-sialyl Lewis X/A (sLeX/A) HECA-452 (a) or anti-L-selectin (CD62L) (b) and analyzed by flow cytometry. PBMC were also stained with anti-CD19, anti-IgD, anti-CD27, Gal-9 and anti-Gal-9; and naïve (IgD+/CD27−), IgM memory (IgD+/CD27+) and memory (IgD−/CD27+) B cell subsets (c) were analyzed for Gal-9 ligand (d) by flow cytometry. Control rhGal-9 staining consisted of 100 mM lactose (Lac) in the buffers (e) and (f). Experiments were repeated on at least 3 donors.

FIGS. 3A-3F show that IFN-treated human vascular EC express a high level of Gal-9. HUVEC were incubated with IFN-0 and/or IFN-γ or TNF-α and analyzed with anti-Gal-9 (a) or anti-E-selectin (b) by flow cytometry. Untreated or IFN-β/-γ-treated HUVEC were analyzed with anti-Gal-9 (d), anti-Gal-1 (e) or anti-Gal-3 (f) with or without a control 50 mM lactose pretreatment. Experiments were repeated on at least 3 donors and statistical significance was ascertained by a Mann-Whitney test—***p<0.001).

FIGS. 6A-6E show that Gal-9 upregulates expression of B cell immunoregulatory factor, SLAMF7. RT-qPCR analysis of SLAMF7 and RHOA was performed on MACS-sorted CD19+ B cells from PBMC incubated with Gal-9 (a). Flow cytometric analysis of SLAMF7 was performed on MACS-sorted tonsillar naïve B cells incubated with Gal-9 (b). RT-qPCR analysis of SLAMF7 and RHOA and Western blot analysis of SLAMF7 were performed on MACS-sorted tonsillar naïve B cells incubated with Gal-9 (c). RT-qPCR analysis of SLAMF7 and RHOA and Western blot analysis of SLAMF7 was also performed on MACS-sorted tonsillar naïve B cells incubated with Gal-9 and a confluent monolayer of HUVEC (d) or with a confluent monolayer of IFN-β/γ-stimulated HUVEC (e). Graphed expression data from at least 5 donors are presented as Fold Change (SEM) of control non-Gal-9-treated B cells (a-c) or of control B cells incubated with untreated HUVEC (d-e) (Unpaired t-test—*p<0.001, p<0.01, *p<0.05).

DETAILED DESCRIPTION OF THE INVENTION

Figure 1A:
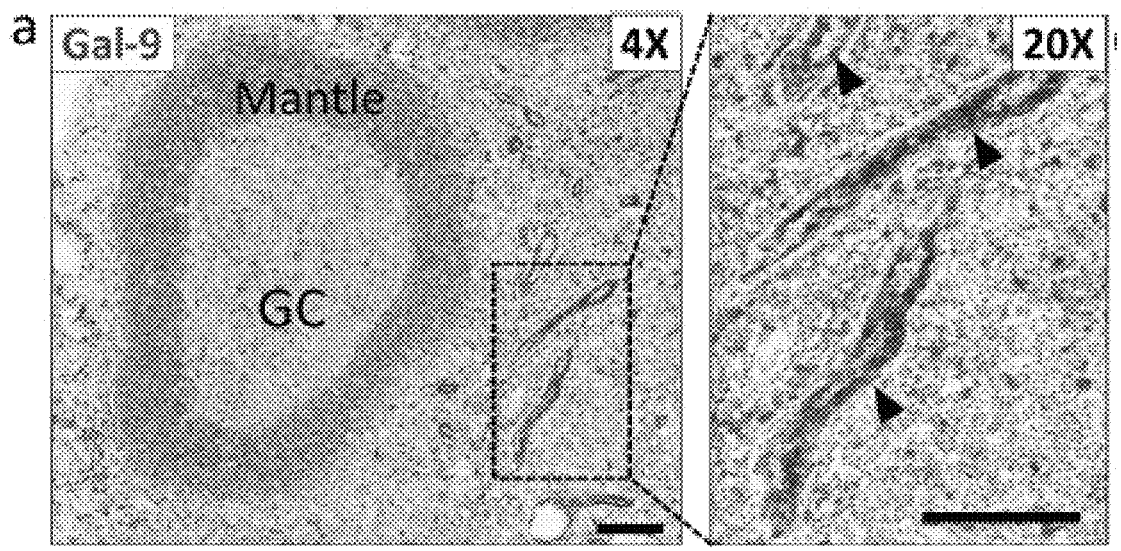
FIGS. 1A-1D show Gal-9 co-localizes with vascular structures in human LN and tonsil. (a) IHC staining of sections of FFPE-tonsil tissues with anti-Gal-9 (brown) and counterstained with hematoxylin showed strong Gal-9 staining in naïve B cells of the mantle as well as in high endothelial venules (HEV) (black arrows). (b) Dual IHC staining of FFPE-tonsil sections with anti-Gal-9 (red) and anti-PAX (brown) and counterstained with hematoxylin showed high Gal-9 expression on EC of HEVs (white arrows) and spatial localization with parenchymal and circulating B cells undergoing diapedesis (insert). (c) IHC staining of serial sections of FFPE-human LN and tonsil sections with either anti-Gal-9 (brown) or anti-PNAd (brown) and then counterstained with hematoxylin demonstrated co-localization of Gal-9 with PNAd+ vessels (black arrows). (d) Dual IF staining of FFPE-tonsil sections with anti-Gal-9 (teal), anti-PNAd (red) and DAPI (blue) showed co-localization of Gal-9 with PNAd+ vessels (insert). All experiments consisted of staining with isotype Ab control (Iso) or secondary Ab alone to control for non-specific staining. Images are representative from at least 5 biological and experimental replicates. Micron bars=100 µm.

The subject invention provides novel strategies, methods, and compositions for treating B cell malignancies and restricting the progression of B cell malignancies, in particular, B cell derived cancers, for example, non-Hodgkin's lymphoma, Hodgkin's lymphoma, chronic lymphocytic leukemia, mantle cell lymphoma and multiple myeloma (MM). Additional B-cell derived cancers that can be treated according to the subject invention, include, for example, B-cell prolymphocytic leukemia, lymphoplasmacytic leukemia, splenic marginal zone lymphoma, marginal zone lymphoma (extra-nodal and nodal), plasma cell neoplasms (e.g., plasma cell myeloma, plasmacytoma, monoclonal immunoglobulin deposition diseases, heavy chain diseases), and follicular lymphoma (e.g., Grades I, II, III, or IV). In a specific embodiment, the subject invention provides compositions and methods for treating MM.

In one embodiment, the subject invention provides a method for treating a B cell malignancy using a combination therapy. In one embodiment, said treatment comprises the administration of a B cell regulator, e.g., a galectin molecule, to a subject suffering from a B cell malignancy, and wherein the subject received, receives or will receive a treatment with a conventional treatment for such B cell malignancy.

In one embodiment, the treatment is applied to a specific group of subjects suffering from a B cell malignancy, wherein the subjects are undergoing, or indicated for, a treatment with a conventional B cell therapy, e.g., immunotherapy. The galectin treatment may be performed during the same period of time as the B cell treatment, or alternatively is done before or after. The latter can be preferable in order to avoid stacking of adverse effects. The person of skill understands that the inventive result is achieved when the physiological effects of a B cell treatment and a galectin overlap, or are combined in a subject in need of such a treatment. It is not necessary to administer the combination as a mixture of both agents. Using the galectin in sequential therapeutic cycles instead of at the same time, the medical practitioner can achieve a combination of the clinical effects of both treatments. Thus, sequential administration regimes fall under the meaning of a combination therapy in accordance with the present invention.

In a preferred embodiment, the treatment of the invention comprises the concomitant or sequential administration of a B cell regulator, e.g., a galectin molecule, and an agent of immunotherapy, e.g., a monoclonal antibody.

In one embodiment, the method involves the binding of B cells to a B cell regulator, e.g., a galectin molecule, which can modulate the Ab responses. Advantageously, such binding of the regulator to B cells impacts B cell immunity and improves the efficacy of targeted therapies against B cell malignancies. The immunoregulator promotes B cell-endothelial cells (EC) interactions to help control B cell reactivity.

In some embodiments, a B cell malignancy treated using the methods of the subject invention is associated with the expression of one or more B cell specific antigens such as, for example, CD3d, CD5, CD6, CD9, CD19, CD20, CD21, CD22, CD23, CD24, CD27, CD28, CD37, CD38, CD40, CD45, CD46, CD48, CD53, CD69, CD70, CD72, CD73, CD79a, CD79b, CD80, CD81, CD83, CD85a, CD85d, CD85e, CD85 h, CD85i, CD85J, CD85k, CD86, CD96, CD98, CD100, CD121 b, CD124, CD127, CD132, CD150, CD152, CD154, CD157, CD166, CD169, CD179a, CD179b, CD180, CD185, CD196, CD197, CD205, CDw210a, CD213a1, CD257, CD267, CD268, CD269, CD274, CD275, CD276, CD278, CD279, CD300a, CD300c, CD307, CD314, CD316, CD317, CD319, CD320, CDw327, and CD331. In a particular embodiment, a cancer treated using the methods of the invention is associated with the expression of CD319.

In one embodiment, the antibody of the antibody therapy is a monoclonal antibody that specifically binds B cell specific antigens, e.g., CD319. In a specific embodiment, the antibody is Elotuzumab (Elo). In one embodiment, the monoclonal antibody that specifically binds B cell specific antigens is, for example, CD38. In a specific embodiment, the antibody is Daratumumab™.

The term "galectin molecule" as used herein refers to a member of the galectin family of secreted galectins. Included are galectin-1, -2, -3, -4, -5, -6, -7, -8, -9, -10, -11, -12, -13, -14 and -15. The nucleotide and amino acid sequences for human and/or other species, e.g., rat, sheep, and rabbit, of these known galectins are available from public databases.

In a specific embodiment, the galectin molecule is selected from galectin (Gal)-1, -3, and -9. In a preferred embodiment, the galectin is Gal-9. Gal-9 can suppress human naïve B cell activation, proliferation and signaling under T-dependent and T-independent activation conditions. Some prominent lymphocyte immunoregulatory genes modulated by Gal-9 include: SLAMF7, FCRL4, CCL22, DUSP8, CCL4, SIGLEC10, FCER2, ZEB1, PPP1R26, GAB2 and DOK37.

Among these genes, signaling lymphocytic activation molecule F7 (SLAMF7 also known as CS1, CRACC or CD319) on human circulating and naïve B cells is significantly induced. SLAMF7 is a type-1 membrane protein that functions as a homotypic adhesion molecule (selfligand) eliciting cell-cell interactions and profound effects on lymphocyte signaling, including a promising immunotherapeutic target on malignant Ab-producing B cells or multiple myeloma.

Regarding SLAMF7 (CD319, CS1 and CRACC) as a therapeutic target, it is the 7th member of the SLAM family of type-1 membrane protein receptors principally expressed on immune cells that transmit cell activating or inhibitory signals. They function characteristically as homotypic receptors in trans and elicit their activating/inhibitory activity depending on co-expression of cytosolic adaptor proteins. SLAM receptors, including SLAMF7, recruit SLAM-associated protein (SAP) family adaptors, namely Ewing sarcoma-associated transcript (EAT)-2, SH2-domain containing protein tyrosine phosphatases (SHP)-1 and SHP-2, and/or SH2-domain containing inositol phosphatase (SHIP)-1 upon homophilic binding to its self-ligand on other immune cells. SLAMF7 is expressed on natural killer (NK) cells, T cells, naive/activated/GC B cells, plasma cells, and macrophages.

In one embodiment, the subject invention provides a pharmaceutical composition comprising 1) a nucleic acid sequence that encodes a Gal protein or a nucleic acid sequence that encodes a protein sharing at least 50%, 55%, 60%, 65%, 70%, 75%, 80%, 85%, 90%, 95%, 96%, 97%, 98% or 99% identity with the Gal protein, 2) an amino acid sequence of a Gal protein, biologically-active fragments, variants thereof, or an amino acid sequence sharing at least 50%, 55%, 60%, 65%, 70%, 75%, 80%, 85%, 90%, 95%, 96%, 97%, 98% or 99% identity with the Gal protein, 3) a vector comprising a nucleic acid sequence that encodes a Gal protein or a nucleic acid sequence that encodes a protein sharing at least 50%, 55%, 60%, 65%, 70%, 75%, 80%, 85%, 90%, 95%, 96%, 97%, 98% or 99% identity with the Gal protein, 4) a cell that overexpresses a nucleic acid sequence of a Gal protein or a nucleic acid sequence that encodes a protein sharing at least 50%, 55%, 60%, 65%, 70%, 75%, 80%, 85%, 90%, 95%, 96%, 97%, 98% or 99% identity with the Gal protein, and/or 5) a cell that overexpresses an amino acid sequence of a Gal protein, biologically-active fragments, variants thereof, or an amino acid sequence sharing at least 50%, 55%, 60%, 65%, 70%, 75%, 80%, 85%, 90%, 95%, 96%, 97%, 98% or 99% identity with the Gal protein.

In one embodiment, the pharmaceutical composition further comprises an antibody that specifically binds to a B cell specific antigen, such as SLAMF7.

The subject invention provides a pharmaceutical composition comprising 1) a nucleic acid sequence that encodes Gal-9 or a nucleic acid sequence that encodes a protein sharing at least 50%, 55%, 60%, 65%, 70%, 75%, 80%, 85%, 90%, 95%, 96%, 97%, 98% or 99% identity with Gal-9, 2) an amino acid sequence of Gal-9 protein, biologically-active fragments, variants thereof, or an amino acid sequence sharing at least 50%, 55%, 60%, 65%, 70%, 75%, 80%, 85%, 90%, 95%, 96%, 97%, 98% or 99% identity with Gal-9, 3) a vector comprising a nucleic acid sequence that encodes Gal-9 or a nucleic acid sequence that encodes a protein sharing at least 50%, 55%, 60%, 65%, 70%, 75%, 80%, 85%, 90%, 95%, 96%, 97%, 98% or 99% identity with Gal-9, 4) a cell that overexpresses a nucleic acid sequence of Gal-9 or a nucleic acid sequence that encodes a protein sharing at least 50%, 55%, 60%, 65%, 70%, 75%, 80%, 85%, 90%, 95%, 96%, 97%, 98% or 99% identity with Gal-9, and/or 5) a cell that overexpresses an amino acid sequence of Gal-9 protein, biologically-active fragments, variants thereof, or an amino acid sequence sharing at least 50%, 55%, 60%, 65%, 70%, 75%, 80%, 85%, 90%, 95%, 96%, 97%, 98% or 99% identity with Gal-9.

In one embodiment, the composition further comprises an antibody that specifically binds to a surface antigen of MM cells, such as SLAMF7.

In one embodiment, the pharmaceutical composition of the subject invention may further comprise one or more therapeutic agents. The therapeutic agent may comprise a chemotherapeutic agent, immunotherapeutic agent or interferon (IFN)), gene therapy and/or radio therapeutic agent. The therapeutic agent may further comprise other cytotoxic agents such as anti-tumour peptides, cytokines and growth factors, and/or cancer vaccines.

Depending on the intended mode of administration, the compounds used in the methods described herein may be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. Each dose may include an effective amount of a compound used in the methods described herein in combination with a pharmaceutically acceptable carrier and, in addition, may include other medicinal agents, pharmaceutical agents, carriers, adjuvants, diluents, etc.

In one embodiment, the composition according to the subject invention also comprises a pharmaceutically acceptable carrier. "Pharmaceutically acceptable carrier" refers to a diluent, adjuvant or excipient with which the antigen disclosed herein can be formulated. Typically, a "pharmaceutically acceptable carrier" is a substance that is non-toxic, biologically tolerable, and otherwise biologically suitable for administration to a subject, such as an inert substance, added to a pharmacological composition or otherwise used as a diluent, adjuvant or excipient to facilitate administration of the composition disclosed herein and that is compatible therewith. Examples of carriers suitable for use in the pharmaceutical compositions are known in the art and such embodiments are within the purview of the invention.

The compositions of the present invention can be administered to the subject being treated by standard routes, including the local, oral, ophthalmic, nasal, topical, intratumoural, transdermal, intra-articular, parenteral (e.g., intravenous, intraperitoneal, intradermal, subcutaneous or intramuscular), intracranial, intracerebral, intraspinal, intravaginal, intrauterine, or rectal route. Additionally, the composition may be administered directly into the tumor of melanoma. Depending on the condition being treated, one route may be preferred over others, which can be determined by those skilled in the art.

Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The proper fluidity can be maintained, for example, by the use of a coating such as lecithin, by the maintenance of the requited particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the pharmaceutical compositions are formulated into ointments, salves, gels, or creams as generally known in the art.

In one embodiment, the method for treating B cell malignancies of a subject, e.g., MM, comprises administering to the subject a pharmaceutically effective amount of 1) a nucleic acid sequence that encodes a Gal protein or a nucleic acid sequence that encodes a protein sharing at least 50%, 55%, 60%, 65%, 70%, 75%, 80%, 85%, 90%, 95%, 96%, 97%, 98% or 99% identity with the Gal protein, 2) an amino acid sequence of a Gal protein, biologically-active fragments, variants thereof, or an amino acid sequence sharing at least 50%, 55%, 60%, 65%, 70%, 75%, 80%, 85%, 90%, 95%, 96%, 97%, 98% or 99% identity with the Gal protein, 3) a vector comprising a nucleic acid sequence that encodes a Gal protein or a nucleic acid sequence that encodes a protein sharing at least 50%, 55%, 60%, 65%, 70%, 75%, 80%, 85%, 90%, 95%, 96%, 97%, 98% or 99% identity with the Gal protein, 4) a cell that overexpresses a nucleic acid sequence of a Gal protein or a nucleic acid sequence that encodes a protein sharing at least 50%, 55%, 60%, 65%, 70%, 75%, 80%, 85%, 90%, 95%, 96%, 97%, 98% or 99% identity with the Gal protein, and/or 5) a cell that overexpresses an amino acid sequence of a Gal protein, biologically-active fragments, variants thereof, or an amino acid sequence sharing at least 50%, 55%, 60%, 65%, 70%, 75%, 80%, 85%, 90%, 95%, 96%, 97%, 98% or 99% identity with the Gal; and administering to the subject an antibody that specifically binds to a B cell specific antigen.

The term "subject" or "patient," as used herein, describes an organism, including mammals such as primates, to which diagnosis, prevention, assessment, and/or treatment according to the present invention can be provided. Mammalian species that can benefit from the disclosed methods of treatment include, but are not limited to, apes, chimpanzees, orangutans, humans, monkeys; domesticated animals such as dogs, cats; live-stocks such as horses, cattle, pigs, sheep, goats, and chickens; and other animals such as mice, rats, guinea pigs, and hamsters.

The terms "treatment" or any grammatical variation thereof (e.g., treat, treating, etc.), as used herein, includes but is not limited to, the application or administration to a subject (or application or administration to a cell or tissue from a subject) with the purpose of delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of a pathology or condition, including any objective or subjective parameter such as abatement; remission; lessening of the rate of worsening; lessening severity of the disease; stabilization, diminishing of symptoms or making the pathology or condition more tolerable to the subject; or improving a subject's physical or mental well-being.

In one embodiment, the method for treating B cell malignancies of a subject, e.g., MM, may comprise administering to the subject a pharmaceutically effective amount of 1) a nucleic acid sequence that encodes Gal-9 or a nucleic acid sequence that encodes a protein sharing at least 50%, 55%, 60%, 65%, 70%, 75%, 80%, 85%, 90%, 95%, 96%, 97%, 98% or 99% identity with Gal-9, 2) an amino acid sequence of Gal-9 protein, biologically-active fragments, variants thereof, or an amino acid sequence sharing at least 50%, 55%, 60%, 65%, 70%, 75%, 80%, 85%, 90%, 95%, 96%, 97%, 98% or 99% identity with Gal-9, 3) a vector comprising a nucleic acid sequence that encodes Gal-9 or a nucleic acid sequence that encodes a protein sharing at least 50%, 55%, 60%, 65%, 70%, 75%, 80%, 85%, 90%, 95%, 96%, 97%, 98% or 99% identity with Gal-9, 4) a cell that overexpresses a nucleic acid sequence of Gal-9 or a nucleic acid sequence that encode a protein sharing at least 50%, 55%, 60%, 65%, 70%, 75%, 80%, 85%, 90%, 95%, 96%, 97%, 98% or 99% identity with Gal-9, and/or 5) a cell that overexpresses an amino acid sequence of Gal-9 protein, biologically-active fragments, variants thereof, or an amino acid sequence sharing at least 50%, 55%, 60%, 65%, 70%, 75%, 80%, 85%, 90%, 95%, 96%, 97%, 98% or 99% identity with Gal-9; and administering to the subject an antibody that specifically binds to SLAMF7.

In one embodiment, the method of treating or reducing the progression of B cell malignancies may further comprise administering to the subject one or more therapeutic agents. The therapeutic agent may comprise a chemotherapeutic agent, immunotherapeutic agent, gene therapy or radio therapeutic agent.

In one embodiment, dosage units containing the nucleic acid and/or peptidic molecules contain about 0.01 mg to 1000 mg, about 0.01 mg to 900 mg, about 0.01 mg to 800 mg, about 0.01 mg to 700 mg, about 0.01 mg to 600 mg, about 0.01 mg to 500 mg, about 0.05 mg to 500 mg, about 0.1 mg to 400 mg, about 0.1 mg to 300 mg, about 0.1 mg to 200 mg, about 0.1 mg to 100 mg, about 0.1 mg to 90 mg, about 0.1 mg to 80 mg, about 0.1 mg to 70 mg, about 0.1 mg to 60 mg, about 0.1 mg to 50 mg, about 0.1 mg to 40 mg, about 0.1 mg to 30 mg, about 0.1 mg to 20 mg, about 0.1 mg to 10 mg, about 0.5 mg to 50 mg, about 1 mg to 40 mg, about 1 mg to 20 mg, about 1 mg to 10 mg, or about 1 mg to 5 mg.

In a specific embodiment, the antibody that specifically binds to SLAMF7 is Elo. Elotuzumab elicits its therapeutic effects by: 1.) Binding to SLAMF7 on MM cells and causing Ab-dependent cellular cytotoxicity (ADCC); 2.) Binding to SLAMF7 on NK cells and activating those cells via SAP engagement of EAT-2 and other downstream extracellular signal-regulated kinase (ERK) pathways; 3.) Binding to SLAMF7 on MM cells and inducing Ab-dependent cellular phagocytosis (ADCP); or 4.) Binding to SLAMF7 on MM cells and inhibiting interactions with its self-ligand on stomal cells in the bone marrow.

The MM cell killing mechanisms via anti-SLAMF7 Ab treatment are all critically dependent on expression of SLAMF7. Advantageously, biological factors, e.g., Gal-9, promotes B cell—EC interactions to help control B cell reactivity and, in the context of cancer therapeutics, upregulate SLAMF7 levels on MM cells to boost therapeutic efficacy of humanized anti-SLAMF7 monoclonal Ab (Elotuzumab).

In one embodiment, the composition may be formulated for administration as tablets, coated tablets, nasal sprays, solutions, emulsions, liposomes, powders, capsules or sustained release forms.

In specific embodiments, the composition of the subject invention may be administered at least once a day, twice a day, or three times a day for consecutive days, e.g. 2, 3, 4, 5, 6, 7, 8, 9, 10, 11, 12, 13, 14, 15, 16, 17, 18, 19, 20, 21, 22, 23, 24, 25, 26, 27, 28, 29, or 30 days. The composition of the subject invention may also be administered for weeks, months or years.

In one embodiment, the methods according to the subject invention may further comprise a step of determining the levels of one or more immunoregulators (e.g., SLAMF7, FCRL4, CCL22, DUSP8, CCL4, SIGLEC10, FCER2, ZEB1, PPP1R26, GAB2, DOK37, I-branched glycans, and/or i-linear glycans) in a sample of the subject prior to the administration and/or after the administration.

A further embodiment of the invention provides a method for monitoring the effect of a treatment for B cell malignancies, such as MM, in a subject.

In one embodiment, the subject invention provides a method for increasing the level of one or more immunoregulators, e.g., SLAMF7, FCRL4, CCL22, DUSP8, CCL4, SIGLEC10, FCER2, ZEB1, PPP1R26, GAB2, and DOK37, in MM cells, the method comprising contacting the MM cells with a composition according to the subject invention. In a further embodiment, the method comprises contacting the MM cells with 1) a nucleic acid sequence that encodes Gal-9 or a nucleic acid sequence that encodes a protein sharing at least 50%, 55%, 60%, 65%, 70%, 75%, 80%, 85%, 90%, 95%, 96%, 97%, 98% or 99% identity with the Gal-9; 2) an amino acid sequence of Gal-9 protein, biologically-active fragments, variants thereof, or an amino acid sequence sharing at least 50%, 55%, 60%, 65%, 70%, 75%, 80%, 85%, 90%, 95%, 96%, 97%, 98% or 99% identity with Gal-9; and/or 3) a vector comprising a nucleic acid sequence that encodes Gal-9 or a nucleic acid sequence that encodes a protein sharing at least 50%, 55%, 60%, 65%, 70%, 75%, 80%, 85%, 90%, 95%, 96%, 97%, 98% or 99% identity with Gal-9. Such method results in an overexpression of one or more immunoregulators in the MM cells.

In one embodiment, the subject invention provides a method for treating a B cell malignancy that is resistant to known therapies, e.g., immunotherapy-resistant MM, in a subject, the method comprising administering to the subject a pharmaceutical composition of the subject invention. Preferably, the composition comprises 1) a nucleic acid sequence that encodes Gal-9 or a nucleic acid sequence that encodes a protein sharing at least 50%, 55%, 60%, 65%, 70%, 75%, 80%, 85%, 90%, 95%, 96%, 97%, 98% or 99% identity with Gal-9, 2) an amino acid sequence of Gal-9 protein, biologically-active fragments, variants thereof, or an amino acid sequence sharing at least 50%, 55%, 60%, 65%, 70%, 75%, 80%, 85%, 90%, 95%, 96%, 97%, 98% or 99% identity with Gal-9, and/or 3) a vector comprising a nucleic acid sequence that encodes Gal-9 or a nucleic acid sequence that encodes a protein sharing at least 50%, 55%, 60%, 65%, 70%, 75%, 80%, 85%, 90%, 95%, 96%, 97%, 98% or 99% identity with Gal-9.

In one embodiment, the subject invention further provides a method for increasing/enhancing/improving the sensitivity of a subject having MM to a treatment, e.g., immunotherapy, the method comprising administering to the subject a pharmaceutical composition of the subject invention.

In one embodiment, the subject invention provides a method for slowing the malignant transformation, the method comprising contacting the MM cells with a composition comprising 1) a nucleic acid sequence that encodes Gal-9 or a nucleic acid sequence that encodes a protein sharing at least 50%, 55%, 60%, 65%, 70%, 75%, 80%, 85%, 90%, 95%, 96%, 97%, 98% or 99% identity with Gal-9, 2) an amino acid sequence of Gal-9 protein, biologically-active fragments, variants thereof, or an amino acid sequence sharing at least 50%, 55%, 60%, 65%, 70%, 75%, 80%, 85%, 90%, 95%, 96%, 97%, 98% or 99% identity with Gal-9, and/or 3) a vector comprising a nucleic acid sequence that encodes Gal-9 or a nucleic acid sequence that encodes a protein sharing at least 50%, 55%, 60%, 65%, 70%, 75%, 80%, 85%, 90%, 95%, 96%, 97%, 98% or 99% identity with Gal-9.

In a further embodiment, the MM cells are resistant to one or more immunotherapies using antibodies selected from, for example, antibodies to SLAMF7, FCRL4, CCL22, DUSP8, CCL4, SIGLEC10, FCER2, ZEB1, PPP1R26, GAB2, and DOK37.

In one embodiment, the subject invention provides a method for improving the sensitivity of MM cells to an immunotherapy, the method comprising contacting the MM cells with a composition of the subject invention and administering the immunotherapy. Preferably, the composition comprises 1) a nucleic acid sequence that encodes Gal-9 or a nucleic acid sequence that encodes a protein sharing at least 50%, 55%, 60%, 65%, 70%, 75%, 80%, 85%, 90%, 95%, 96%, 97%, 98% or 99% identity with Gal-9, 2) an amino acid sequence of Gal-9 protein, biologically-active fragments, variants thereof, or an amino acid sequence sharing at least 50%, 55%, 60%, 65%, 70%, 75%, 80%, 85%, 90%, 95%, 96%, 97%, 98% or 99% identity with Gal-9, and/or 3) a vector comprising a nucleic acid sequence that encodes Gal-9 or a nucleic acid sequence that encodes a protein sharing at least 50%, 55%, 60%, 65%, 70%, 75%, 80%, 85%, 90%, 95%, 96%, 97%, 98% or 99% identity with Gal-9.

In one embodiment, the subject invention provides a method for improving the sensitivity of MM cells to anti-SLAMF7 Ab, the method comprising contacting the MM cells with a composition of the subject invention, and applying the anti-SLAMF7 Ab. Preferably, the composition comprises 1) a nucleic acid sequence that encodes Gal-9 or a nucleic acid sequence that encodes a protein sharing at least 50%, 55%, 60%, 65%, 70%, 75%, 80%, 85%, 90%, 95%, 96%, 97%, 98% or 99% identity with Gal-9, 2) an amino acid sequence of Gal-9 protein, biologically-active fragments, variants thereof, or an amino acid sequence sharing at least 50%, 55%, 60%, 65%, 70%, 75%, 80%, 85%, 90%, 95%, 96%, 97%, 98% or 99% identity with Gal-9, and/or 3) a vector comprising a nucleic acid sequence that encodes Gal-9 or a nucleic acid sequence that encodes a protein sharing at least 50%, 55%, 60%, 65%, 70%, 75%, 80%, 85%, 90%, 95%, 96%, 97%, 98% or 99% identity with Gal-9.

In one embodiment, the subject invention provides a method for improving the therapeutic efficacy of an antibody that specifically binds to SLAMF7, e.g., Elo, in treating MM in a subject, the method comprising administering to the subject a pharmaceutically effective amount of 1) a nucleic acid sequence that encodes Gal-9 or a nucleic acid sequence that encodes a protein sharing at least 50%, 55%, 60%, 65%, 70%, 75%, 80%, 85%, 90%, 95%, 96%, 97%, 98% or 99% identity with Gal-9, 2) an amino acid sequence of Gal-9 protein, biologically-active fragments, variants thereof, or an amino acid sequence sharing at least 50%, 55%, 60%, 65%, 70%, 75%, 80%, 85%, 90%, 95%, 96%, 97%, 98% or 99% identity with Gal-9, 3) a vector comprising a nucleic acid sequence that encodes Gal-9 or a nucleic acid sequence that encodes a protein sharing at least 50%, 55%, 60%, 65%, 70%, 75%, 80%, 85%, 90%, 95%, 96%, 97%, 98% or 99% identity with Gal-9, 4) a cell that overexpresses a nucleic acid sequence of Gal-9 or a nucleic acid sequence that encodes a protein sharing at least 50%, 55%, 60%, 65%, 70%, 75%, 80%, 85%, 90%, 95%, 96%, 97%, 98% or 99% identity with Gal-9, and/or 5) a cell that overexpresses an amino acid sequence of Gal-9 protein, biologically-active fragments, variants thereof, or an amino acid sequence sharing at least 50%, 55%, 60%, 65%, 70%, 75%, 80%, 85%, 90%, 95%, 96%, 97%, 98% or 99% identity with Gal-9, prior to the administration of the antibody that specifically binds to SLAMF7 in the subject.

A "nucleic acid" according to the invention refers to polynucleotides, such as DNA, RNA, modified DNA, modified RNA as well as mixtures thereof.

As used herein, "variants" of a protein refer to sequences that have one or more amino acid substitutions, deletions, additions, or insertions. In preferred embodiments, these substitutions, deletions, additions or insertions do not materially adversely affect the protein activity. Variants that retain one or more biological activities are within the scope of the present invention.

"Fragments" and its variants are also within the scope of proteins of the subject invention, so long as the fragment retains one or more biological properties. Preferably, the fragment is at least 10%, 15%, 20%, 25%, 30%, 35%, 40%, 45%, 50%, 55%, 60%, 65%, 70%, 75%, 80%, 85%, 90%, 95%, 96%, 97%, 98%, or 99% of the full length protein, e.g., Gal-9.

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," and "comprise" can be used interchangeably; "consisting essentially of," and "consists essentially of" can be used interchangeably; and "consisting," and "consists" can be used interchangeably.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Where particular values are described in the application and claims, unless otherwise stated the term "about" meaning within an acceptable error range for the particular value should be assumed.

When ranges are used herein, such as for dose ranges, combinations and subcombinations of ranges (e.g., subranges within the disclosed range), specific embodiments therein are intended to be explicitly included.

EXAMPLES

Materials and Methods
Cells.

Peripheral blood mononuclear cells (PBMCs) were isolated from normal healthy donor leukopacks (Children's Hospital Blood Donor Center, Boston, MA; OneBlood, Inc., Miami, FL) and tonsillar mononuclear cells were isolated from discarded tonsil specimens provided by Nicklaus Children's Hospital (Miami, FL) using Histopaque-1077 (Sigma-Aldrich, Milwaukee, WI) gradient centrifugation and then stored in liquid nitrogen for future use in flow cytometry and in B cell isolation, adhesion and transcriptional analyses. To isolate resting naïve B cells, PBMC aliquots were thawed, washed and subjected to a combination of immunomagnetic bead cell separation kits: Human Naïve B cell Isolation Kit II and CD27 MicroBeads Kit (Miltenyi Biotec, Auburn, CA). To validate B cell and naïve B cell isolation, PBMCs and resting naïve B cell isolates were stained with a combination of anti-CD3-APCCy7, anti-CD19-PerCP, anti-CD27-PECy7, anti-IgD-APC and Zombie Green viability dye (Biolegend, San Diego, CA) and analyzed by flow cytometry, confirming purity of IgD+/CD19+/CD27-naïve B cells of >95%.

Flow Cytometry of L-Selectin, Sialyl Lewis X and Gal-9 Ligands.

PBMCs were stained with a T cell or B cell antibody panel as follows. T cell panel: anti-CD3-PE Cy7 (Biolegend), anti-human CD4-PerCP (Biolegend), anti-CD45RO-APC Cy7(Biolegend), anti-CD62L-PE (Biolegend) and either biotin-anti-sialyl Lewis X (Clone HECA-452) (BD Biosciences, San Jose, CA) and streptavidin-APC (BD Biosciences) or recombinant human Gal-9 (rhGal-9) (R&D Systems, Minneapolis, MN)±100 mM lactose (ThermoFisher Scientific, Haverhill, MA) and anti-human Gal-9-APC (Biolegend). B cell panel: anti-human CD19-PerCP (Biolegend), anti-CD3-APC Cy7 (Biolegend), anti-CD14-APC Cy7 (Biolegend), anti-CD27-PE Cy7 (Biolegend), anti-human IgD-FITC (Biolegend), anti-CD62L-PE and either biotin-anti-sialyl Lewis X (Clone HECA-452) and streptavidin-APC or rhGal-9±100 mM lactose and anti-human Gal-9-APC. For panels assessing sialyl Lewis X and L-selectin, PBMCs (106/50 μl), biotin-anti-sialyl Lewis X (Clone HECA-452) and anti-CD62L-PE were incubated for 45 min to 1 h at 4° C. in a low binding 96-well plate, washed with FACS buffer (HBSS, 2% FCS, 10 mM HEPES, 2 mM EDTA), incubated with streptavidin-APC for 30 min at 4° C., washed with FACS buffer and then transferred and fixed in PBS/1% paraformaldehyde. For panels assessing Gal-9 ligand, PBMCs (106/100 μl) and rhGal-9±100 mM lactose in PBS/1% BSA in a low-binding 96-wellplate were incubated for 45 min to 1 hr on ice, washed, incubated with anti-human Gal-9-APC 45 min on ice, washed, incubated with other primary antibodies 45 min on ice, washed and then transferred and fixed and stored in PBS/i % paraformaldehyde until analysis. Please note that all incubations and washes for Gal-9 ligand assay were ±100 mM lactose. Flow cytometry was performed on a FACSCanto (BD Biosciences, San Jose, CA) and analyzed using either Diva (version 8.0.1, BD Biosciences) or FlowJo software (version 7.6.5, FlowJo LLC, Ashland, OR).

Flow Cytometry of Gal-1, Gal-3, Gal-9 and SLAMF7.

Resting naïve B cells were stained separately with either anti-human Gal-9-APC (Biolegend), anti-Gal-3-PE Cy7 (Biolegend) or anti-Gal-1 (Invitrogen/Thermo Fisher Scientific, Waltham, MA) plus goat anti-mouse IgG-FITC (Southern Biotech)±100 mM lactose (Sigma-Aldrich). Human umbilical vein endothelial cells (HUVEC), including those incubated for 24-72 h with TNF-α (10 ng/ml), IFN-β (60 ng/ml), IFN-γ (20 ng/ml) or IFN-β (60 ng/ml) and IFN-γ (20 ng/ml), were stained for Gal-1, Gal-3 or Gal-9 as follows: Using a low-binding 96-well plate, HUVEC (106/50 μl PBS/l % BSA) harvested with 0.5 mMEDTA and washed in HBSS were incubated with anti-human Gal-1 (Invitrogen/Thermo Fisher, Waltham, MA) or mouse IgG1 (Biolegend) with anti-Gal-3-PE Cy7 (Biolegend) or control rat IgG2a-PE Cy7 (Biolegend); or with anti-human Gal-9-APC (Biolegend) or control mouse IgG1-APC (Biolegend) for 45 min on ice and washed. To control for endogenous carbohydrate-dependent Gal binding, control groups were prepared in parallel, wherein all incubations and washes included 100 mM lactose. Samples stained with conjugated antibodies were transferred and fixed and stored in PBS/1% paraformaldehyde until analysis. Samples stained with unlabeled antibodies (anti-human Gal-1 and mouse IgG1) were resuspended in goat anti-mouse IgG-FITC (Southern Biotech, Birmingham, AL), incubated 45 min on ice, washed and then fixed and stored in PBS/l % paraformaldehyde until analysis. Flow cytometry was performed on a FACSCanto as above.

For detection of cell surface SLAMF7, resting naïve B cells, including cells incubated for 16 hr with 4 μg/ml hrGal-9 (R&D Systems), were washed and stained with PE-anti-human SLAMF7 (Abeam). Flow cytometry was performed using BD FACSCelesta™ (BD Biosciences).

Immunohistochemical and Immunofluorescence Staining.

FFPEhuman LN and tonsil specimens were obtained through the Dana Farber/Harvard Cancer Center Specialized Histopathology and Pathology Specimen Locator Services and stained for Gal-9, PAX5 or peripheral node addressin (PNAd) using a Leica automated staining platform as follows. For immunohistochemical (IHC) staining of Gal-9, sections were subjected to antigen retrieval on Lecia Bond H1(30) (Citrate) for 30 min, incubated with mouse anti-human Gal-9 antibody (10 μg/mL; Clone 9M1-3; Biolegend) or isotype control (10 μg/mL; Biolegend) diluted in Leica antibody diluent for 30 min, incubated anti-mouse secondary antibody-HRP conjugates and developed with DAB (Leica Bond Refine Detection Kit). For dual IHC staining of PAX5 following Gal-9 staining, sections were stained with rabbit anti-PAX5 antibody (1:50; clone D19F8; Cell Signaling Technology) or isotype control (10 μg/mL; Biolegend) and detected using the Leica Bond Polymer Refine Red Detection Kit, post primary alkaline phosphatase (AP) for 15 min at room temperature, and polymer-AP for 20 min at room temperature. For PNAd IHC staining, sections were subjected to EDTA antigen retrieval for 30 min, incubated with rat anti-PNAd antibody (1:100; Clone MECA-79; Biolegend) or isotype control (10 μg/mL; Biolegend) diluted in Leica antibody diluent for 30 min, incubated anti-rat secondary antibody-HRP conjugates, developed with DAB (Leica Bond Refine Detection Kit). All IHC stained sections were counterstained in hematoxylin.

For immunofluorescent analysis of PNAd and Gal-9, FFPE tissue sections were sequentially subjected to EDTA antigen retrieval and incubated with rat anti-PNAd (1:100; clone MECA-79) using the Leica Biosystems Refine Detection Kit, secondary anti-rat Ab HRP conjugate (Vector Labs) and Alexa Fluor™ 594 Tyramide Reagent (Invitrogen/Thermo Fisher) and then subjected to citrate antigen retrieval and incubated with mouse anti-human Gal-9 (10 μg/mL; clone 9M1-3; Biolegend) using the Leica Biosystems Refine Detection Kit and OPAL™-690 Tyramide Reagent (Perkin Elmer). PNAd was imaged in Texas red with red pseudo color and Gal-9 was imaged in Cyanine 5 with teal pseudo color on the Thermo Fisher EVOS microscope.

Gene Expression Profile Analysis.

Data mining and gene expression comparative analysis of murine LN stromal and immune cells was performed using the GEO dataset (GSE15907; www.ImmGen.org). Data demonstrated that murine ECs in uninflamed and inflamed skin-draining LN express a high level of LGALS9 relative to those levels in murine naïve B cells. Box plots illustrated 3-4-fold higher LGALS9 levels in skin-draining LNs (SLN) compared with Gal-9 in naïve B cells.

Global Transcriptome Analysis.

Resting human naïve B cell isolates were treated with 50 mM lactose on ice for 30 min, washed twice with media and then incubated overnight in 24-well plates using RPMI-1640/10% FCS/2 mM L-glutamine, 1000 Units/ml penicillin/streptomycin. There were four treatment groups included in the overnight cultures: 1.) Buffer alone, 2) 1 μg/ml rhGal-9 (R&D Systems), 3) 1 μg/ml rhGal-9+50 mM lactose and 4) 50 mM lactose alone. After 16 hrs, cultured cells were harvested and subjected to a Dead Cell Removal kit (Miltenyi Biotec) prior to staining for flow cytometric analysis and isolating RNA using RNeasy Plus Mini kits (Qiagen, Hilden, Germany). RNA samples were submitted to the Dana-Farber Cancer Institute Molecular Biology Core Facilities (Boston, MA) for RNA-seq analysis.

For library preparation, libraries were prepared using Roche Kapa mRNA HyperPrep sample preparation kits from 100 ng of purified total RNA according to the manufacturer's protocol. The finished dsDNA libraries were quantified by Qubit fluorometer, Agilent TapeStation 2200, and RT-qPCR using the Kapa Biosystems library quantification kit according to manufacturer's protocols. Uniquely indexed libraries were pooled in equimolar ratios and sequenced on an Illumina NextSeq500 with single-end 75 bp reads. For RNAseq analysis, sequenced reads were aligned to the UCSC hg19 reference genome assembly and gene counts were quantified using STAR (v2.5.1b). Differential gene expression testing was performed by DESeq2 (v1.10.1) and normalized read counts (FPKM) were calculated using cufflinks (v2.2.1). RNA-seq analysis was performed using the VIPER snakemake pipeline. Expression raw data can be accessed at the NCBI site in the GEO repository with a GEO accession number of GSE160678.

RT-qPCR Analysis.

To confirm Gal-9-dependent gene regulation identified by RNASeq analysis, additional experiments were performed incubating 4 µg/ml rhGal-9 with sorted human naïve B cell isolates. B cells were incubated with 4 µg/ml rhGal-9 (R&D Systems), 50 mM lactose or buffer control for 16 hr, washed 2× with PBS, pelleted and lysed for RNA extraction in Buffer RLT (Qiagen). Alternatively, cultures of resting or IFN-γ/β-activated HUVEC (72 hrs) were incubated for 16 hr with sorted naïve B cells and buffer control. B cells were carefully aspirated, washed 2× with PBS, pelleted and lysed for RNA extraction in Buffer RLT (Qiagen). RNA was isolated per manufacturer protocol. SuperScript™ VILO™ cDNA synthesis kit (Invitrogen) was used to covert isolated RNA to cDNA. Real Time-quantitative PCR (RT-qPCR) was then performed using TaqMan Fast master mix (ThermoFisher Scientific) and TaqMan primers to amplify genes, SLAMF7 (AssID: Hs00904275_m1), EAT2 (AssID: Hs01592483_m1), RHOA (AssID: Hs00357608_m1) and internal control 18s (AssID: Hs03003631_g1). Assays included 20 ng cDNA/sample and TaqMan master mix was used according to manufacturer's protocol. For every donor analyzed, each gene was run in triplicate.

Adhesion Assays.

Early passage HUVEC were grown in T-75 flasks using R&D Endothelial Cell Growth Base Media with growth supplement (R&D Systems). Cells were harvested with trypsin/EDTA (0.53 mM), washed and replated at 200,000 cells/well/1.5 ml in 12-well plates. HUVEC were incubated at 37° C. for 1-2 h and, where indicated, then incubated for 24-72 h with fresh media containing IFN-β (180 ng/ml; Peprotech) and/or IFN-γ (60 ng/ml; Peprotech). Prior to the assay, 1 µg/ml rhGal-9 (R&D Systems) with or without 50 mM lactose (ThermoFisher Scientific) was added to HUVEC cultures for 30 min. MACS-sorted human B cells suspended at $10^6$/ml in 1 µg/ml hrGal-9 were added to confluent HUVEC cultures for 1 hr, wells were washed 2×, and bound cells were fixed in 3% glutaraldehyde and counted under phase contrast microscopy. Cell counts were tabulated from a minimum of 6 fields from a field of view at 20× magnification per well/3 wells over ≥4 experiments and graphed as mean±SEM.

For assays conducted under physiologic shear flow conditions, early-passaged HUVEC were plated into microchambers (IbiTreat µ-Slide VI0.4, Ibidi, Germany) at 50,000 cells/channel/30 µL. Microchambers were incubated 24-48 h with fresh HUVEC media (R&D systems). Microchamber channels were loaded with fresh HUVEC media containing 1 µg/ml rhGal-9 (R&D Systems) with or without 50 mM Lactose for 1 hr prior to assay. MACS-sorted human B cells suspended at $2\times10^6$ cells/mL were mixed with HUVEC media containing 1 µg/ml rhGal-9 (R&D Systems) with or without 50 mM lactose for 30 min prior to loading into chamber channels. Microchambers were secured using an AMEP-VH021 dual-slide vessel holder (Thermo Fisher Scientific) and visualized with an EVOS M7000 imaging system (Thermo Fisher Scientific).

B cells were drawn into the chamber channels using a Harvard Apparatus PhD 2000 Series pump with 10 cc syringe and allowed to sediment for <4 min. B cells were then subjected to pre-programmed increasing shear stress video-recorded at 10× with adherent B cells tabulated from a minimum of duplicate channels over ≥5 experiments and graphed as mean±SEM.

Migration Assays.

To assess B cell migration, HUVEC were cultured on transwells (Corning) with 3 µm pore size for 72 h. MACS-sorted CD19 B cells from PBMC were plated in the top chamber and B cell chemoattractant CXCL13 (R&D Systems) was added to the bottom chamber. Where indicated, 4 µg/ml hrGal-9 (R&D Systems) was added to the top chamber with or without 50 mM lactose (inhibitor of galectin-glycan binding). B cells were allowed to migrate for 24 h and the B cells that migrated to the bottom chamber were collected and counted using a hemocytometer.

Immunoblotting.

MACS-sorted CD19+ B cells from PBMC or tonsillar naïve B cell isolates were incubated with 4 µg/ml hrGal-9 with/without HUVEC or incubated with IFN-stimulated HUVEC monolayer. After 24 h, B cells were collected and lysed in RIPA buffer (Pierce, Inc.) with protease and phosphatase inhibitors (Thermo-Fisher Scientific, Inc.). Cells were incubated on ice for 30 min and centrifuged at 10000 RPM for 10 min at 4° C. The supernatant was collected, and protein concentration was quantified using BCA (ThermoFisher Scientific). Equal amounts of protein from each sample was prepared with denaturing sample buffer (ThermoFisher Scientific). Samples were boiled for 5 min and loaded on a 4-12% gradient SDS-PAGE gel (Bio-Rad) and subjected to electrophoresis. Separated proteins were then transferred to PVDF membrane (Merk Millipore, Inc.), blocked for 1 hr and incubated with primary antibodies to pFAK (Cell Signaling), FAK (Cell Signaling), human SLAMF7 (Abcam), human EAT-2 (Abcam), pERK (Cell Signaling), ERK (Cell Signaling) and β-actin (Abcam) overnight. Membranes were washed and incubated with IRDye®-conjugated anti-rabbit or mouse secondary antibodies (LI-COR) for 1 h at RT. Blots were then analyzed using a LI-COR Imager (LI-COR Biosciences, Lincoln, NE).

Statistics.

Statistical analysis was done using GraphPad Prism: Mann-Whitney test, unpaired two-tailed t-test and/or paired t-test.

Example 1—High Endothelial and Post-Capillary Venules are Rich in Galectin (Gal)-9

Gal-9 has a profound intrinsic and extrinsic effect on the activation and proliferation of naïve B cells. Functional observations were obtained using murine B cells deficient in Gal-9 or incubations of soluble recombinant human Gal-9 (Gal-9) with human naive B cells. Considering the putative regulatory role for extrinsic Gal-9, the native spatial and cellular expression patterns of Gal-9 in peripheral LN is incomplete.

Figure 1B:
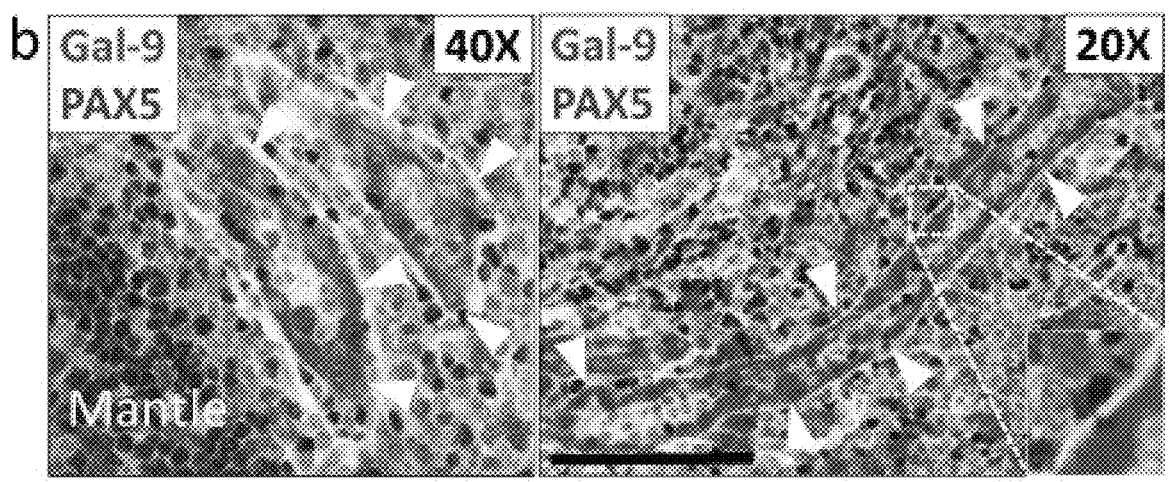
Figure 1C:
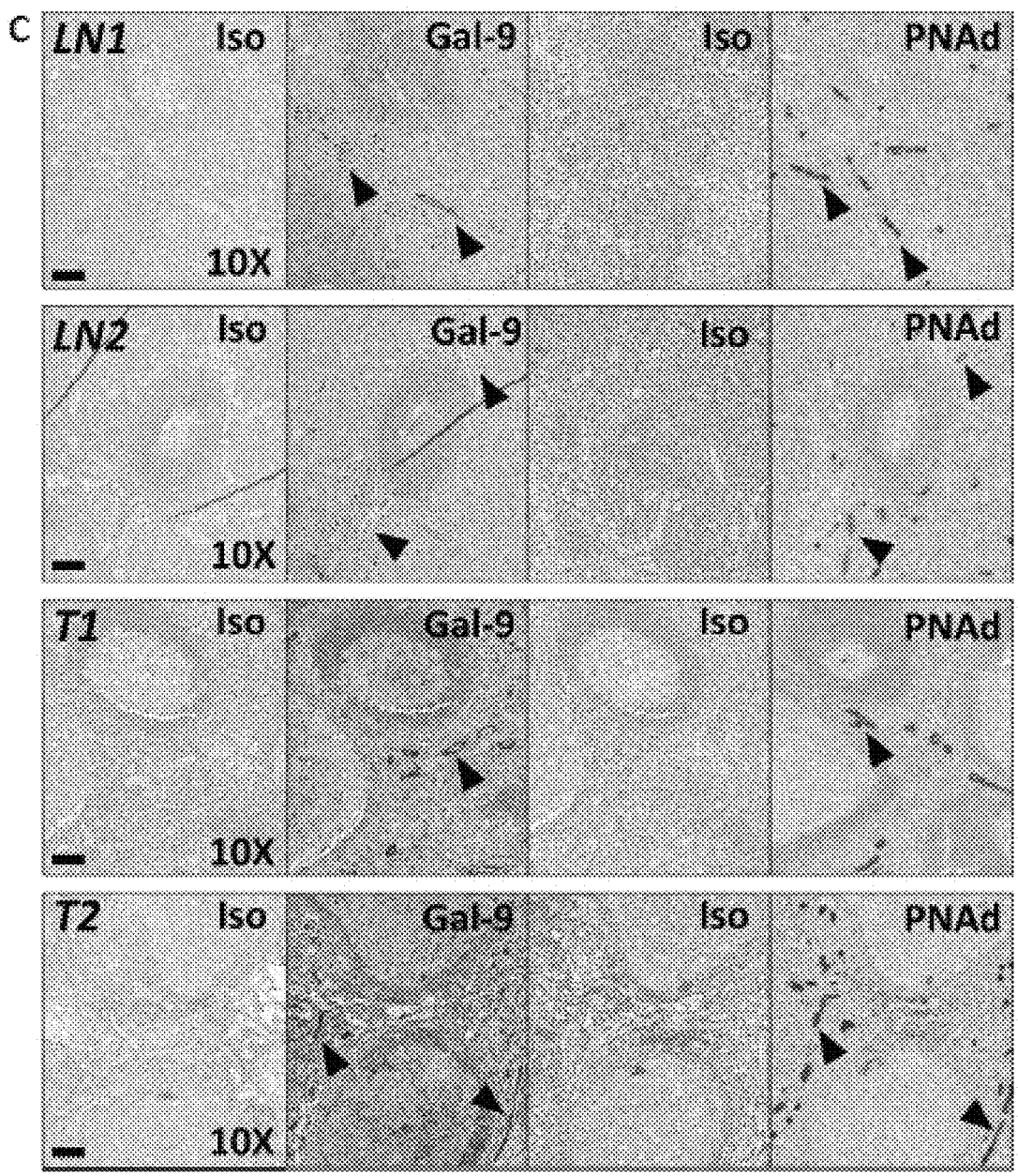

To identify cells and LN structures bearing Gal-9, immunohistochemistry (IHC) of Gal-9 was performed on formalin-fixed, paraffin embedded (FFPE)-human 'reactive' tonsils and LN tissues. Gal-9 staining indicated the expected expression of Gal-9 in mantle region of B cell follicles that are predominated by naïve B cells, but there was also robust staining on vascular structures (FIG. 1a). Double IHC staining of Gal-9 (red) and B cell marker PAX5 (brown) indicated that Gal-9 was indeed expressed on endothelial cells (EC) of post-capillary venules and high endothelial venules (HEV) that was distinct from B cell staining (FIG. 1b). IHC of Gal-9 or of peripheral LN addressin (PNAd), a luminal marker of high endothelial venules, on serial sections of LNs revealed co-localization of Gal-9 and PNAd (FIG. 1e).

Figure 1D:
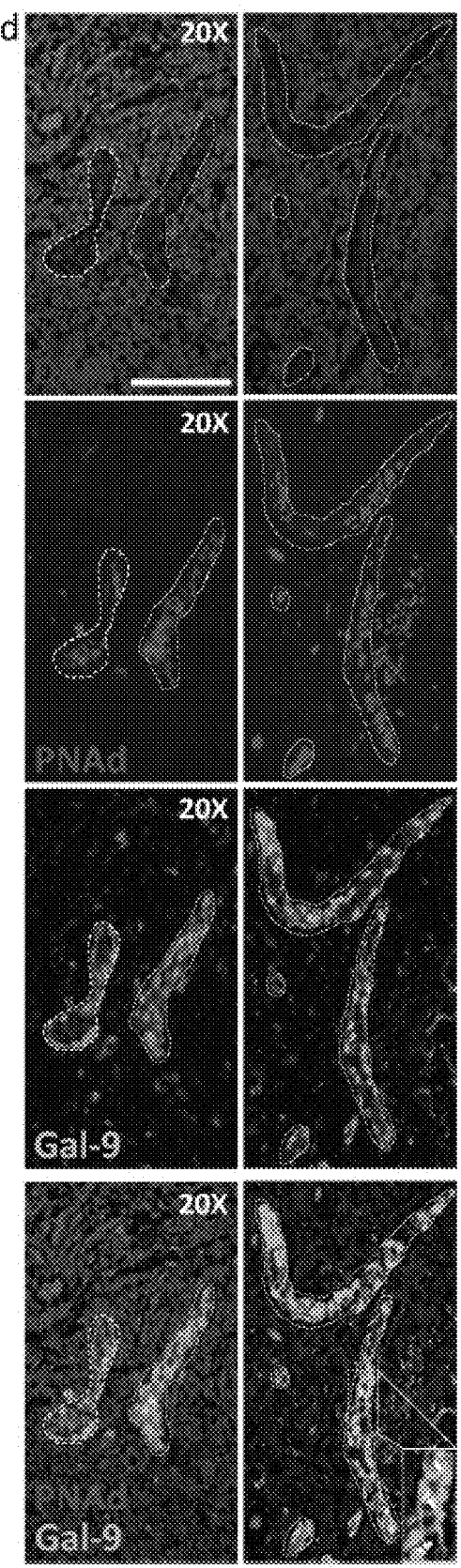

To further address co-localization, dual immunofluorescence (IF) analysis of Gal-9 (teal) and PNAd (red) on FFPE-human tonsil sections was performed and demonstrated that Gal-9 was conspicuously expressed in and on ECs of HEV, including co-localization with PNAd on the luminal aspect of the HEV (white) (FIG. 1d). Incidentally, high expression of Gal-9 (LGALS9) was also evident from gene mining data (www.ImmGen.org), showing that resting and inflamed skin-draining murine LN expressed LGALS9 at a 3- and 4-times higher level, respectively, than that of naïve B cells. In all, these data suggested that vascular Gal-9 expression in the peripheral LN may be a major source of Gal-9 to bind and modulate naïve and memory B cells that express high levels of counter-receptor Gal-9 ligand.

To determine whether EC-derived Gal-9 promotes circulating and naïve B cell retention in PLN while regulating B cell activity, including the upregulation of SLAMF7, PLN homing assays are performed in WT and Gal-9-deficient (Gal-9−/−) mice to dissect role of B cell-derived or EC-derived Gal-9. The major Gal-9-binding receptors on human ECs mediating adhesion to investigate molecular mechanism of how Gal-9 bridges Gal-9 receptors on both B cells and vascular ECs. These adhesion, homing, and Gal-9 ligand ID assessments are followed up with investigations on how Gal-9-binding increases SLAMF7 expression on human naïve B cells and whether elevations in SLAMF7 engage SAP inhibitory receptors, SHP-1/-2 or SHIP-1, and/or promote cell proliferation.

To study the role of Gal-9 in B cell homing, homing assays are performed in C57/BL-6 WT and Gal-9−/− mice. Donor WT or Gal-9−/− B cell homing to naïve or inflamed PLNs are assayed in recipient WT or Gal-9−/− mice. This tests that vascular Gal-9 is a key factor to B cell adhesion/homing to PLN.

Naïve B cells are isolated from spleens of WT or Gal-9−/− mice by mechanical dissociation using negative selection MACS technology (Miltenyi) and purity (>90%) confirmed by FACS assay with anti-CD19. Following labeling with Cell Tracker™ Green, B cells ($10^6$) are i.v. transferred into WT or Gal-9−/− mice. To induce inflammation and Gal-9-inducing cytokine IFN-γ73, recipient mice will be painted on abdomens with 2 doses of 0.5% 2,4-dinitrofluorobenzene (DNFB). After 1 and 24 hr, PLNs (auricular, axillary, brachial, inguinal) or inguinal LNs for DNFB scenario are mechanically dissociated and B cells analyzed by FACS with PE-B220 and "green" channel. Importantly, PBMC will also be isolated and analyzed for donor cell pools to assess circulating donor cell reservoirs.

Moreover, in control experiments to compare relative contribution of L-selectin and Gal-9, anti-mouse L-selectin moAb Mel-14 is co-administered with donor B cell inocula into WT and Gal-9−/− mice. In other control experiments, FACS is used to assay naïve T cells (anti-CD3/L-selectinhi/CD44lo) to assess efficiency of HEV to recruit host T cells. Relative indexes of donor B cells in LN/PBMC pools are assessed in 8 mice over 3 experiments for statistical significance.

Example 2—Gal-9 Mediates Human B Cell-Vascular EC Adhesion while Reducing TEM

Galectins are secreted lectins that bind and modulate the function of leukocytic, epithelial, mesenchymal and cancer cell surface glycoproteins. By binding β-galactoside-containing glycans, galectins induce glycoprotein lattices/clustering, which modify downstream signaling and survival/death pathways. Gal-9, notably, can bind T cell TIM-3, CD44 and/or protein disulfide isomerase, and avidly to linear poly-LacNAc glycans on B cell CD44 and/or CD45, to downregulate activation pathways and/or effector functions. Interestingly, Gal-9 can also mediate adhesion between human eosinophils and interferon gamma (IFN-γ)-activated fibroblasts and human umbilical vein endothelial cells (HUVEC), indicating that Gal-9 and its dual carbohydrate-recognition domains can bridge cells in trans. Whether Gal-9 can mediate B cell adhesion to vascular ECs is not known.

Inherent expression of lymphocyte adhesion molecules, lymphocyte (L)-selectin and endothelial (E)-/platelet (P)-selectin-binding moieties sialyl Lewis$^X$ and $^A$ involved in lectin-mediated lymphocyte adhesion, juxtaposed to Gal-9 ligand expression on human circulating B cells were evaluated prior to assaying B cell. Comparative expression of L-selectin and E-/P-selectin ligands, which are known for mediating peripheral LN and inflamed tissue homing and commonly high on human naïve and central memory T cells (TCM), respectively, serve as ideal positive controls for assaying relative levels on human circulating B cell subsets. Flow cytometry of circulating T and B cell subsets from PBMC revealed that IgM-memory and memory B cells expressed very little sialyl Lewis antigen and naïve B cells expressed none (FIG. 2a). Moreover, compared with high L-selectin expression on naïve and TCM, circulating naïve B cells expressed 75% less L-selectin (FIG. 2b). As expected, all circulating B cell subsets expressed robust Gal-9-binding activity (Gal-9 ligand) (FIGS. 2c and d) that was inhibited by lactose (FIGS. 2e and f).

Figure 3C:
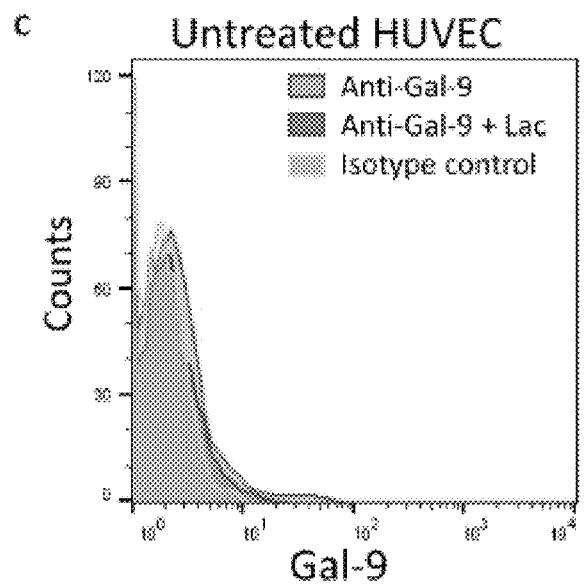
Figure 3D:
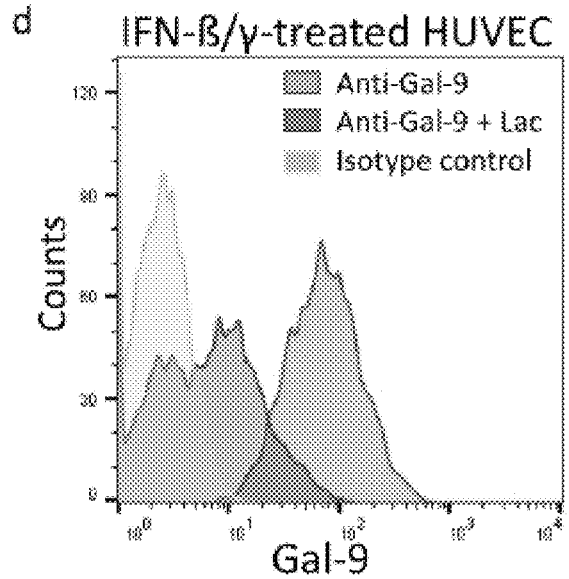
Figure 3E:
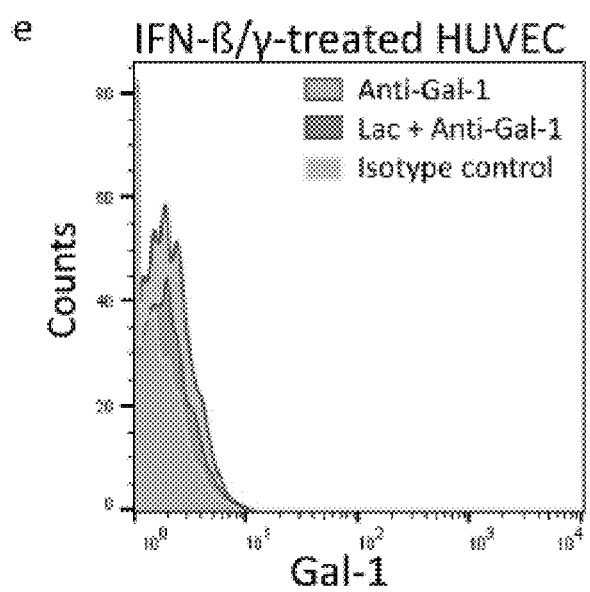
Figure 3F:
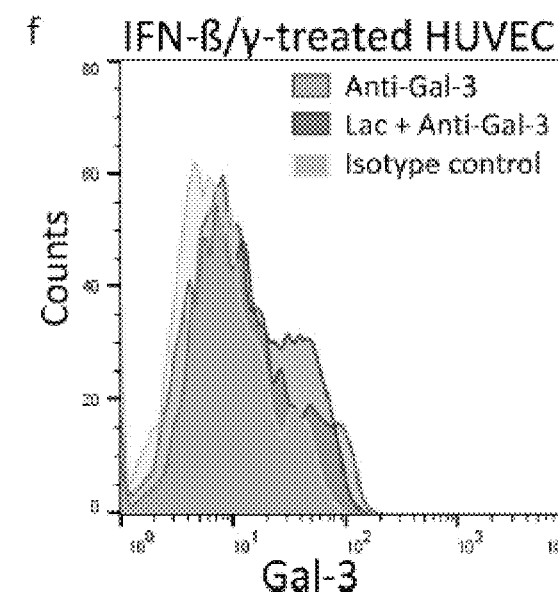

The suitability of HUVEC as a model system was then confirmed by analyzing the inherent EC adhesion molecule expression in conjunction with assessing Gal-9 expression on resting HUVEC, HUVEC incubated with conventional TNF-α, or HUVEC treated with Type 1 IFN-β and/or Type 2 IFN-γ. Compared with TNF-α, incubations with IFN-β and/or IFN-γ caused a significant upregulation of HUVEC surface Gal-9 ($p<0.001$) (FIGS. 3a and d). Moreover, whereas TNF-α induced E-selectin expression, IFN-β and IFN-γ did not upregulate E-selectin expression (FIG. 3b). Interestingly, other well-described galectins, Gal-1 and Gal-3, were not expressed on the surface of IFN-β/γ-treated HUVEC (FIGS. 3e and f). Lactose-containing negative controls confirmed carbohydrate-binding activity of Gal-9.

Figure 4A:
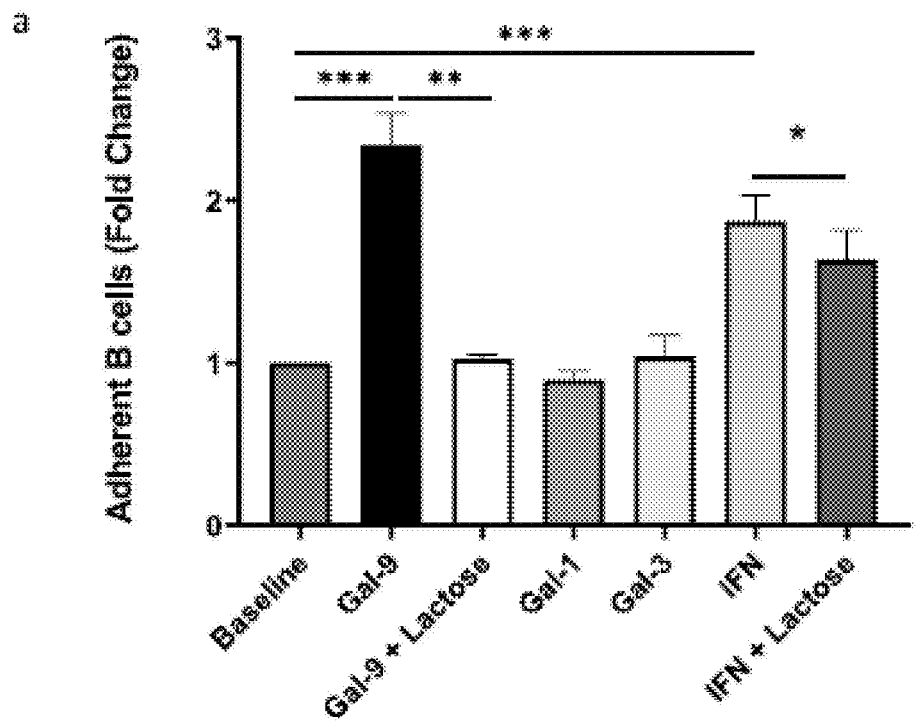
FIGS. 4A-4B show that human circulating B cells adhere to human vascular EC dependent on Gal-9. (a) MACS-sorted CD19+ B cells from PBMC were assayed for adhesion to confluent monolayers of HUVEC. Where indicated, Gal-1, -3 or -9 were added to B cell-HUVEC incubations, 50 mM lactose was added to control for galectin carbohydrate-binding dependency, and IFN-β and -γ pretreatments were imposed to upregulate Gal-9. Experimental data are presented as mean Fold Change (SEM) from baseline B cell adhesion to resting HUVEC from at least 5 independent experiments and donors (Mann-Whitney test—*p<0.001, p<0.01; Paired t-test—*p<0.05). (b) MACS-sorted CD19+ B cells from PBMC were assayed for adhesion to confluent monolayers of HUVEC under shear flow conditions. Where indicated, Gal-9 (with or without 50 mM lactose) was added to cells, cells were infused over into the chamber, shear stress was increased in 0.1 dyn/cm2 every 30 s from 0.2 to 1 dyn/cm2. Data are graphically presented as Adherent Cells (SEM) over a shear stress range from at least 5 independent donors (Paired t-test —**p<0.01).

Assays were first performed by incubating MACS-sorted CD19+ B cells from PBMC over confluent monolayers of HUVEC in the presence/absence of Gal-9 or with Gal-1, Gal-3, or lactose buffer controls. Following a 1 hr incubation at 37° C. and gentle washes, B cells were enumerated from several fields of view at 10× magnification. Compared with baseline adhesion, Gal-9 caused a 2.5-fold increase in adhesion ($p<0.001$) that was completely inhibited in the presence of lactose (FIG. 4a). Moreover, there was no observed increase in B cell adhesion in the presence of Gal-1 or Gal-3. On IFN-stimulated HUVEC, there was a 2-fold increase in B cell adhesion with a decrease in the presence of lactose, suggesting the high Gal-9 levels on IFN-HUVEC may support B cell adhesion (FIG. 4a). Of note, MACS-sorted naïve B cells from tonsil tissue were also assayed in this adhesion assay system and similar fold change increases were noted in Gal-9-treated and IFN-induction groups.

Figure 4B:
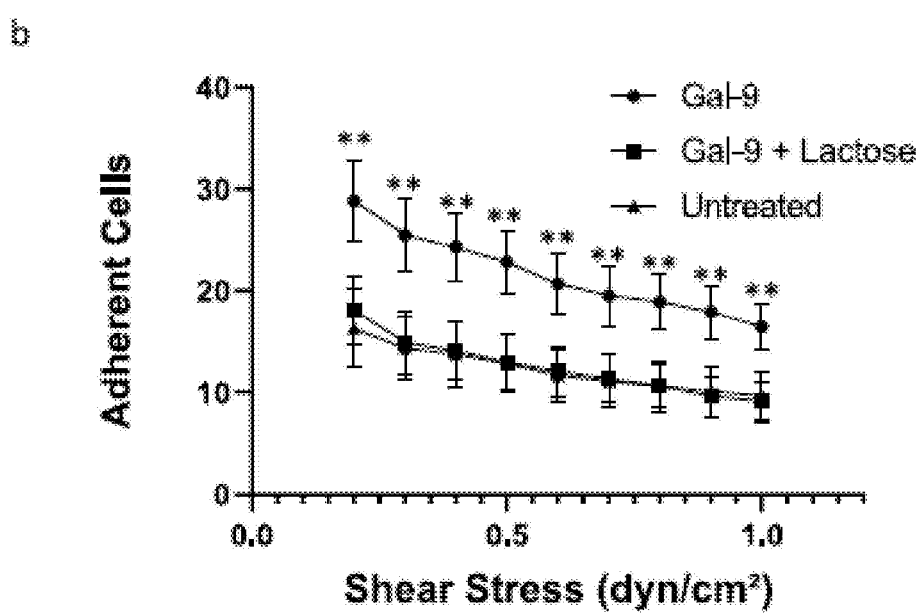

In flow chamber experiments under physiologic shear stress, human perfused over confluent monolayers of HUVEC at a shear stress range up to 2 dyn/cm². Compared with cell suspensions containing lactose, a significant 2-fold increase was observed in shear resistance or cells remaining bound in groups containing Gal-9 (FIG. 4b). While new cell tethers between 0.1 and 1.0 dyn/cm² range with an occasional cell rolling activity were observed, these events were overall rare and transitory, indicative of weak carbohydrate/lectin interactions and not characteristic of selectin-selectin ligand-binding.

Figure 5A:
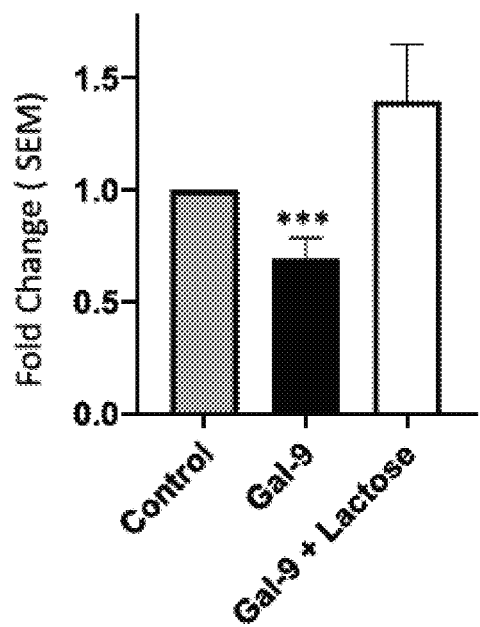
FIGS. 5A-5B show that Gal-9 slows human B cell TEM. (a) MACS-sorted CD19+ B cells from PBMC were incubated with Gal-9 with or without lactose over confluent monolayers of HUVEC for 16 hr in transwell chambers containing CXCL-13 in the bottom chamber. After 16 hr, frequency of B cells in the bottom chamber were enumerated and expressed as Fold Change (SEM) compared with non-Gal-9-treated control. (b) Western blot analysis of pFAK (Tyr397) or of FAK and β-actin controls were performed on unmigrated B cells isolated from the non-Gal-9-treated control or Gal-9-treated wells. Phosphorylated FAK staining intensity data were expressed as Fold Change (SEM) compared with non-Gal-9-treated control. All data are tabulated from at least 3 independent experiments and donors (Unpaired t-test—*p<0.001, p<0.01).
Figure 5B:
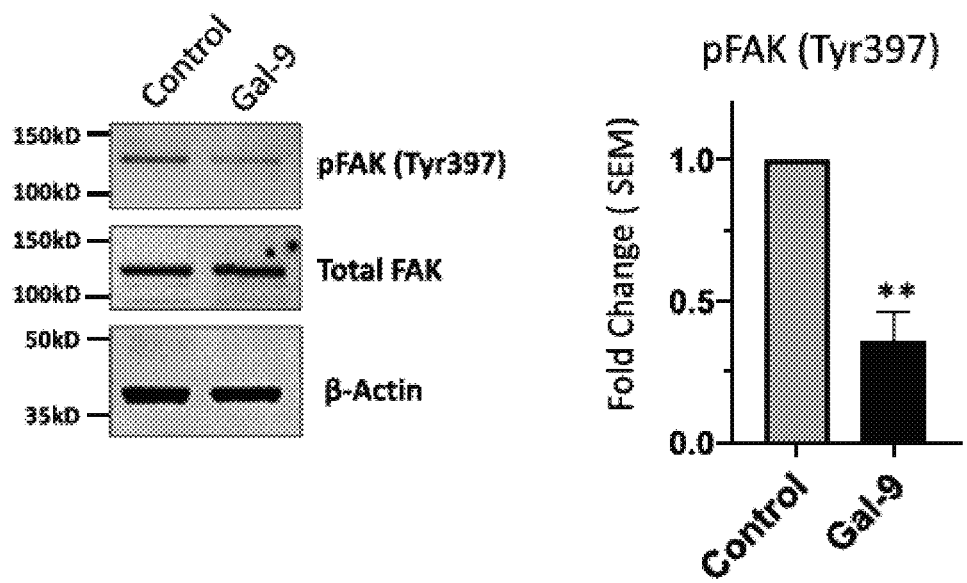

To further assess Gal-9 effects on human B cell-EC dynamics, TEM confluent HUVEC monolayers and B cell chemoattractant CXCL13 in the lower chamber. MACS-sorted CD19+ B cells from PBMC, including Gal-9 with or without lactose, were incubated on HUVEC for 16 hr, and B cells, which underwent TEM, were enumerated in the bottom chamber. Compared with non-Gal-9-treated controls, the mean fold change (SEM) of B cells that underwent TEM was significantly less (40%) in the Gal-9-treated group (p<0.001) (FIG. 5a). This attenuated migratory effect was reversed in co-cultures containing Gal-9 inhibitor lactose (FIG. 5a). In support of this inhibitory effect, activation of focal adhesion kinase (FAK) was assayed by Western blotting and showed that Gal-9 incubations caused a significant reduction (~65%) in phosphorylated Tyr-397 on FAK, which is a protein tyrosine kinase associated with integrin-dependent cellular migration (FIG. 5b). These data implicated Gal-9 as a potentially critical determinant in human B cell-EC interactions, serving to both promote adhesion and decelerate B cell TEM.

Example 3—Gal-9 Globally Regulates Human Naïve B Cell Activation and Differentiation Pathways Gal-9 can suppress human naïve B cell activation, proliferation and signaling under T-dependent and T-independent activation conditions. Based on data here showing Gal-9's role in bridging B cells to ECs, it has been hypothesized that Gal-9-mediated adhesion could globally impact gene expression programs controlling B cell function.

To understand early transcriptional events conferred by extracellular Gal-9-binding, MACS-sorted human naïve B cells were cultured overnight with Gal-9 or with controls: buffer only, Gal-9 and lactose, or lactose alone. Before culturing, cells from all groups were preincubated with lactose buffer to elute any pre-bound endogenous Gal-9 that could elicit outside-in effects. After removing dead cells, RNA from two biological replicates for each group was extracted and analyzed by RNA-seq. Principal component analysis revealed sample variation as well as sample clustering. Gene clustering of Gal-9 group was distinctive from buffer only and lactose groups, suggesting extracellular Gal-9-binding elicited a specific gene expression program. Gene expression levels from Gal-9 and lactose and lactose alone groups clustered together and, in some cases, were dissimilar from Gal-9 and buffer only groups, suggesting that lactose treatment nullified extracellular Gal-9-dependent gene regulation in both groups and may have potentially caused other ancillary events. Heatmap and hierarchical clustering revealed differentially-expressed genes upregulated (red) or downregulated (blue) in the Gal-9 group that were distinguishable from controls. There were many significant gene expression differences noted between Gal-9 and control groups (padj<0.05). In some cases, gene comparisons between Gal-9 and buffer only groups were less pronounced than Gal-9 and Gal-9-lactose groups, suggesting that endogenous Gal-9 could be rapidly mobilized and dispersed to induce outside-in signals. Using gene ontogeny (GO) term enrichment analysis, differentially-expressed upregulated or downregulated genes terms highlighted conspicuous elevation in pathways that dampen cell activation and improve survival and a depression of pathways necessary for intracellular protein, organelle and cytoskeleton dynamics. Some of the prominent lymphocyte immunoregulatory genes modulated by Gal-9 included: SLAMF7, FCRL4, CCL22, DUSP8, CCL4, SIGLEC10, FCER2, ZEB1, PPP1R26, GAB2, DOK3, PEG10, RIMS3 and GSG2. These results suggested that Gal-9 could collectively promote cell quiescence by simultaneously programming anti-activation, pro-survival and cell stasis pathways.

Among many critical genes up- or downregulated by Gal-9-binding, signaling lymphocytic activation molecule F7 (SLAMF7 also known as CS1, CRACC or CD319) in human circulating and naïve B cells functionally intersects immunoregulation and cellular adhesion/dynamics effects. SLAMF7 is a type 1 membrane protein that functions as a homotypic adhesion molecule (self-ligand) eliciting cell-cell interactions and profound effects on lymphocyte signaling. Depending on expression of SLAMF7-associated adaptor proteins (SAP), namely Ewing sarcoma-associated transcript (EAT)-2, SH-2 domain containing protein phosphatases (SHP)-1 and -2 and SH-2 domain containing inositol phosphatase (SHIP)-1, SLAMF7 homophilic interactions can either enhance or obstruct immune cell signaling.

Figure 6E:
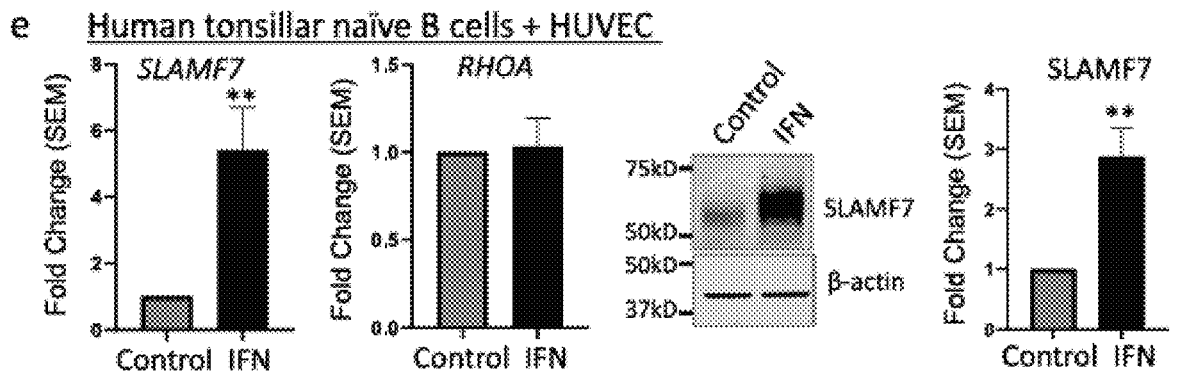

Notably, when SLAMF7 associates with EAT-2, immune cell activation and cytokine production are enhanced, whereas, in the absence of EAT-2, inhibitory signals persist. Here, RT-qPCR, flow cytometric and Western blot analysis of MACS-sorted CD19+ B cells from PBMC treated with Gal-9 confirmed significant upregulation of SLAMF7 mRNA and SLAMF7 protein (p<0.05) (FIGS. 6a and b). This upregulation was also observed when MACS-sorted tonsillar naïve B cells were incubated with Gal-9 (p<0.01) (FIG. 6c), with Gal-9 and HUVEC cultures (p<0.001) (FIG. 6d), or with IFN-stimulated HUVEC (p<0.01) (FIG. 6e). Incidentally, there was no concomitant increase in expression of RHOA, a GTPase associated with promoting cytoskeleton reorganization and cell motility, which supported Gal-9's global influence to restrict cell movement (FIGS. 6a and c-e). These results suggest that soluble Gal-9 and potentially vascular Gal-9 may impact anti-activation, pro-survival and cell dynamics in human circulating and LN-resident naïve B cell pathways and, notably, induce a self-ligand and MM cell target, SLAMF7.

Figure 7A:
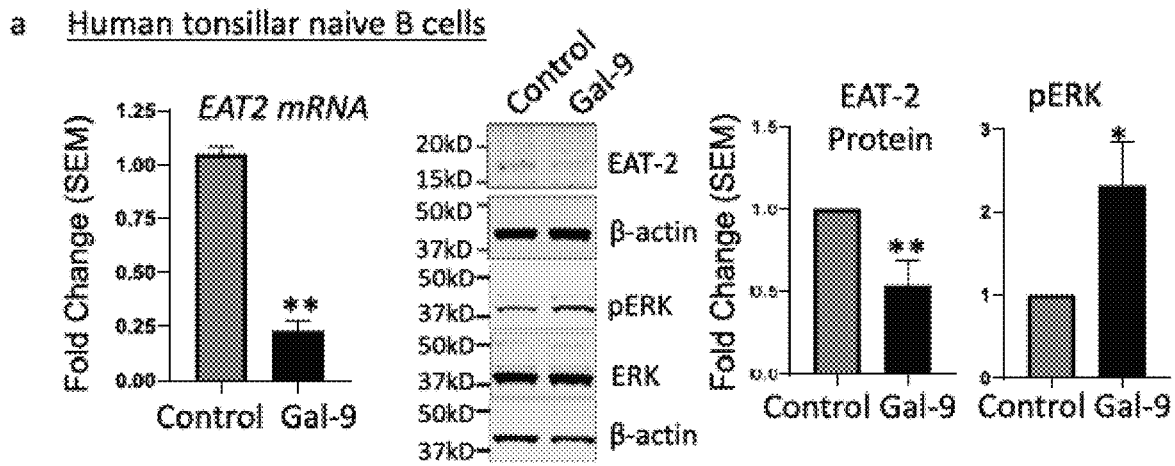
FIGS. 7A-7C show that Gal-9 ablates EAT-2 while increasing activation of pro-survival factor, ERK. RT-qPCR analysis of EAT2 and Western blotting of EAT-2 were performed on MACS-sorted tonsillar naïve B cells incubated with Gal-9 (a). Western blot analysis of pERK, ERK and β-actin was also performed on MACS-sorted tonsillar naïve B cells incubated with Gal-9 (a). RT-qPCR analysis of EAT2 and western blot analysis of pERK, ERK and β-actin was performed in MACS-sorted circulating naïve B cells (b) and unsorted circulating B cells (c) incubated with Gal-9. Graphed expression data from ≥3 donors are presented as Fold Change (SEM) of control non-Gal-9-treated B cells (Unpaired t-test—**p<0.01, *p<0.05).
Figure 7B:
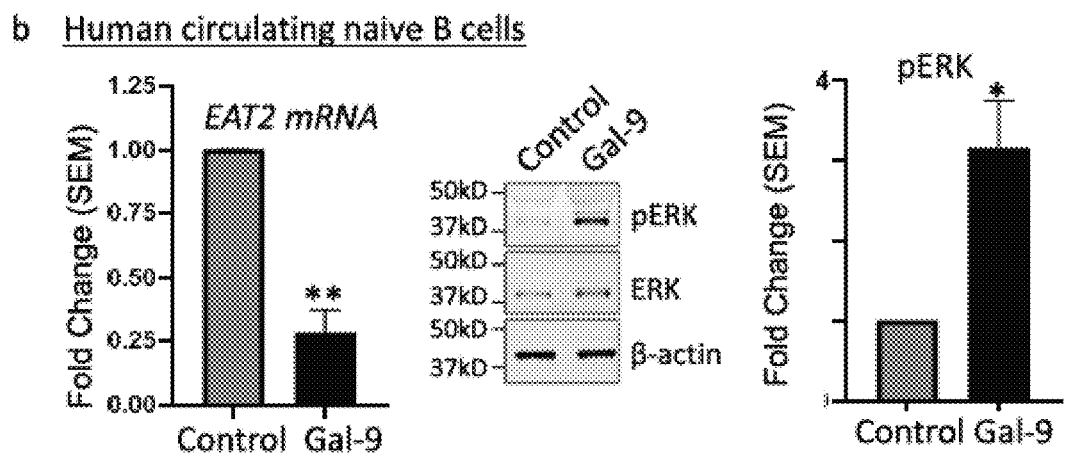
Figure 7C:
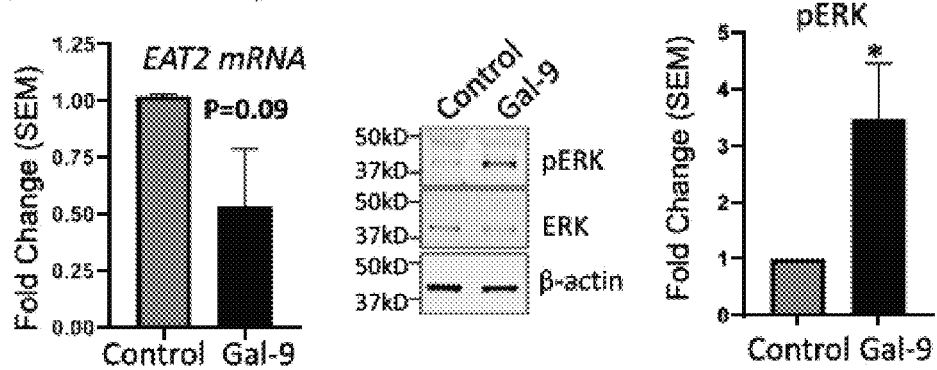

To determine whether SLAMF7 could elicit pro-activation signals, expression of the required SLAMF7-associated adaptor proteins (SAP), e.g., EAT-2, SHP-1/-2 and SHIP-1, was investigated in human naïve B cells incubated with Gal-9. Compared with untreated control, EAT2 mRNA and EAT-2 protein levels assayed by RT-qPCR and Western blotting were strikingly lower in Gal-9-treated tonsillar naïve B cells by as much as 75% and 60%, respectively (p<0.01) (FIG. 7a). These data, which revealed the putative inhibitory consequence of SLAMF7 upregulation, were underscored by the concomitant elevation in pro-survival factor, phosphorylated ERK (FIG. 7a). Furthermore, human circulating naïve B cells displayed significant downregulation of EAT-2 while upregulating pro-survival ERK signaling depicted by enhanced pERK with Gal-9 treatment (p<0.05) (FIG. 7b). Gal-9-treated unsorted human circulating B cells also resulted in a reduction in EAT2 mRNA and elevated pERK levels, though EAT2 downregulation was less significant likely due to component memory B cell populations (FIG. 7c).

Together, these data suggested that exogenous and endogenous Gal-9 could induce SLAMF7 expression and simultaneously ablate EAT-2 and elevate pERK levels in human naïve B cells to provoke SLAMF7-mediated inhibitory signals and cell survival independent of BCR ligation.

Human tonsillar and circulating naïve B cell isolates (n=5 donors each) incubated with 4 g/ml rGal-9 for 16 hr are used. Lysates/RNA is prepared for Western blotting and RT-qPCR assays. In addition to assaying for EAT-2 protein, pro-survival factor, phosphorylated ERK in both tonsil and circulating cell isolates are assessed. Moreover, both inhibitory SHP-1/-2 and SHIP-1 levels are examined by Western blotting and RT-qPCR that are necessary for inhibitory SLAMF-7 activity.

In addition to assessing these phosphatases, cell viability and cell proliferation levels are assessed by FACS analyzing annexin V/PI positivity and Ki-67, respectively, and in human circulating/tonsillar B cell cultures (grown in IL-2/4/-10 stimulated with anti-IgM F(ab)2 treated with/without 1 μg/ml Gal-9 (with/without 50 mM lactose).

Furthermore, to fully appreciate inhibitory/activating of Gal-9-dependent newly-synthesized SLAMF7, treatment of Gal-9-treated cells with rhSLAMF7-Ig (R&D Systems) was imposed prior to assessing cell viability/proliferation. This approach provides information regarding how homophilic SLAMF7-SLAMF7 interactions on SLAMF7$^{hi}$ naive B cells can influence cellular activities.

Example 4—Gal-9 Binding to Human MM Cells can Rapidly Induce the Surface Expression of SLAMF7

Figure 8:
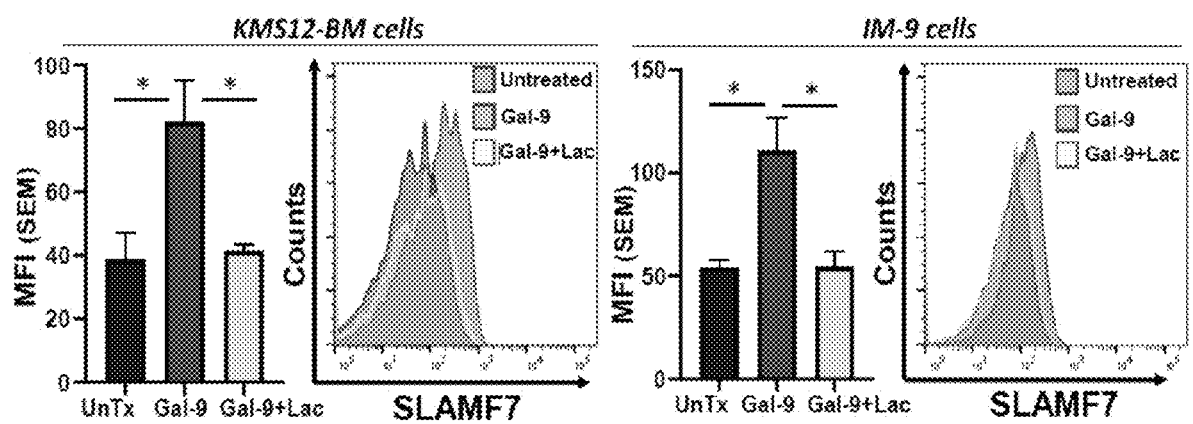
FIG. 8 shows that SLAMF7 is significantly upregulated on human MM cells incubated with Gal-9.

The effects of Gal-9 on human naïve B cells indicate that SLAMF7 is significantly induced on the cell surface. Whether this self-ligand is inhibitory or activating in naïve B cells is unclear. However, one of the more exciting prospects of this observation is the potential of using soluble rGal-9 and an adjuvant therapeutic approach to increase the level of SLAMF7 on MM cells and improve the therapeutic efficacy of anti-SLAMF7 Elotuzumab therapy. To analyze the effects of SLAMF7 on human MM cells, human MM (KMS-12-BM) and (IM-9) cell lines were incubated with 4 μg/ml hrGal-9 with or without 50 mM lactose for 16 h and analyzed by flow cytometry. Compared with SLAMF7 levels on cells treated with buffer control or Gal-9 and 50 mM lactose controls, Gal-9 incubations caused a >2-fold increase in SLAMF7 levels (p<0.05) without an apparent defect on the growth rate of cultures (FIG. 8). These data indicate that Gal-9 can be used to boost expression of the promising target, SLAMF7, on MM cells.

In addition, Gal-9-dependent SLAMF7-induction is confirmed using SLAMF7$^{hi}$, SLAMF7$^{hi}$ IM-9, and SLAMF7-RPMI-8226 MM cell lines under a range of rhGal-1 from 0.1 to 30 μg/ml. Semi-confluent cultures are incubated in buffer control or hrGal-9 with/without 50 mM lactose for 16 h and analyze SLAMF7 levels with Elo Ab as well as death markers, a pro-apoptotic stain Annexin V and dead cell stain, PI by flow cytometry. Using non-growth inhibitory concentrations, RT-qPCR is performed to validate de novo elevation in SLAMF7 mRNA synthesis. These FACS and RT-qPCR assessments are repeated using confluent cultures of IFN-activated (surface Gal-9 hi/Gal-1-/Gal-3-) HUVEC and Gal-9-binding lactose controls incubated 16 hr with human MM cell lines to assess extracellular cell bound Gal-9 effects on MM cell SLAMF7. Importantly, these studies include CD138+-sorted primary human MM cells from patients (n=4) to assess SLAMF7 induction on authentic patient MM cells.

To further assess mechanism of Gal-9-dependent SLAMF7 gene induction, Gal-9's effects on known transcriptional regulators of SLAMF7 gene expression in MM cells are examined. KMS-12-BM cells are treated with SLAMF7-inducing concentrations of rhGal-9 or buffer/lactose controls as above and use ChIP-IT Chromatin Immunoprecipitation Kit (Active Motif) to identify putative MM cell SLAMF7 transcriptional moAbs (Cell Signaling Tech) to IKZF3, in addition to other known SLAMF7 promoter-binding TFs, Aiolos and Blimp-1. Cells will then be fixed in 1% formaldehyde at 37° C. for 5 min and sonicated. After centrifugation, supernatants are incubated with respective TF moAbs for 16 hr at 4° C. Mixtures are subjected to protein A-affinity chromatography and DNA is analyzed by PCR to regions corresponding to TF-binding sites in the SLAMF7 promoter. Initially, due to multiple IKZF3-binding sites, primer pairs are designed to both upstream (-941 to -579) and downstream (-343 to -133) binding sites in the SLAMF7 promoter. These results suggest whether Gal-9-dependent SLAMF7 transactivation is concomitant with SLAMF7 promoter-binding activity of IKZF3. Depending on whether IKZF3, Aiolos and/or Blimp-1 promoter-binding correspond with Gal-9-dependent SLAMF7 induction, the corresponding effects of TF silencing (via shRNA) or cDNA overexpression on Gal-9-dependent SLAMF7 induction are examined in KMS-12-BM. Results from these analyses define IKZF3, Aiolos and/or Blimp-1 are critical for Gal-9-dependent SLAMF7 induction in MM.

Example 5—Analyze Gal-9 Ligand Identity on Human MM Cells

N- and O-glycan metabolic inhibitor and glycosidase treatments are employed to reveal Gal-9-binding determinant. To determine the major glycoprotein receptor(s) of Gal-9 on MM cell, two human MM cell lines, KMS-12-BM, and IM-9, are expended. Harvested cells will be biotinylated (Pierce, Inc.), labeled with rhGal-9 (4 g/ml) with or without negative binding control 50 mM lactose, immunoprecipitated with anti-Gal-9, then Western blotted with streptavidin.

To examine the relative contribution of the identified Gal-9 glycoprotein ligand in cellular Gal-9 binding, gene editing CRISPR-Cas9 technology us employed. Targeting guide sequences to identified membrane protein(s) are cloned into LentiCRISPR V2 (Addgene) and co-transfected in 293T cells with packaging plasmids pMD2.G and psPAX2 (Addgene) using FUGENE 6, and lentivirus harvested after 48 h. KMS-12-BM/IM-9 cells are transduced with 3 ml lentivirus and 8 μg/ml polybrene and cultured overnight. Puromycin is added after 48 h. Depletion of Gal-9 ligand candidate in puro-resistant MM cells is confirmed by FACS.

To determine which glycans confer Gal-9-binding on whole cells, both biochemical and enzymatic modulators of glycosylation are used to target N-glycans, O-glycans and glycolipids. To inhibit N—/O-glycans or glycolipid synthesis, MM cell lines are treated for 72 h with 1 μg/ml α-mannosidase inhibitor Kifunensine, 1 mM Benzyl-O-GalNAc or 2 μM of PPPP (Ronald L. Schnaar, Johns Hopkins U.), respectively, or vehicle controls and assess rhGal-9-binding by FACS. Inhibition is confirmed by FACS with PHA-L lectin (N-glycans) and VVA lectin (O-glycans).

To confirm glycan-dependency on identified Gal-9 glycoprotein ligand, the ligand is immunoprecipitated from human MM cell lines and primary human MM cells and N—/O-glycans are analyzed on the peptide sequence using nanoLC-MS/MS on Thermo Scientific™ Orbitrap Eclipse™ Tribrid™ Mass Spectrometer.

Figure 9:
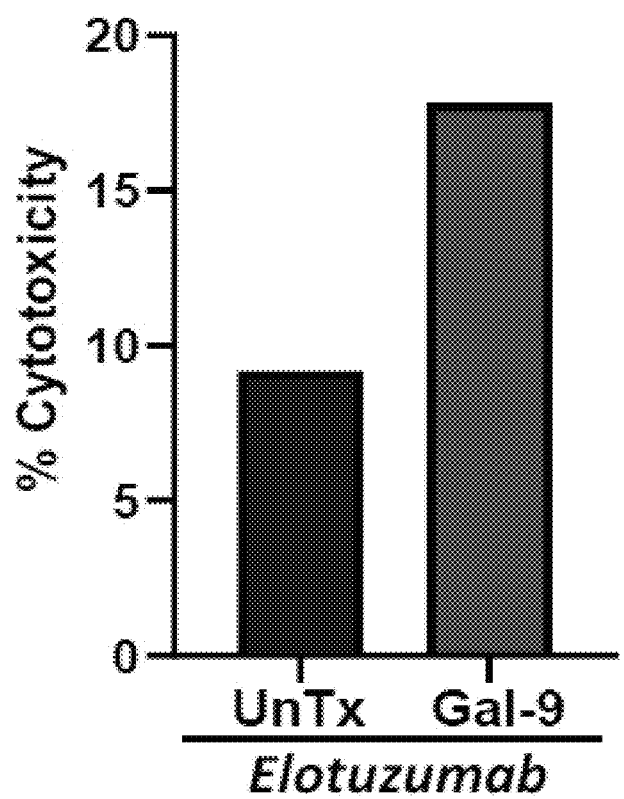
FIG. 9 shows human NK cell lysis of human KMS-12-BM myeloma.

Example 6—Analyze In Vitro Efficacy of Gal-9 and Anti-SLAMF7 Ab on MM Cell Death One of the principal mechanisms of in vivo anti-SLAMF7 inhibitory efficacy on MM cells is via NK-mediated ADCC. To assess whether Gal-9 treatment enhances ADCC activity by upregulating SFAMF7 levels, the following ADCC assay is employed. (+) control human MM IM-9 (SLAMF7 hi), KMS-12-BM (SLAMF7 hi) and (−) control RPMI-8826 (SLAMF7—) are used to assess NK cell-dependent ADCC. MM cells are incubated with 4 µg/ml rhGal-9, rhGal-9 and lactose control, or diluent control for 16 h to induce SLAMF7 expression. NK cells will be isolated from PBMC of normal healthy donors using a Miltenyi CD56 NK cell isolation negative selection kit. Treated MM cells are then incubated with NK cell isolates at a effector to target ratio of 30:19 and a therapeutic range of anti-SLAMF7 Ab (Elotuzumab) or hIgG isotype control concentrations from 0.0001 to 10 µg/ml for 4 h. Cellular cytotoxicity is analyzed using the CytoTox 96 non-radioactive cytotoxicity assay per manufacture's protocol. In the ADCC cell experiment using human NK cell isolates and KMS-12-BM MM cells in conditions above, compared with untreated MM cells (UnTx), Gal-9-treated MM cells doubled Elo-MM cell lysis (FIG. 9). Gal-9 can increase surface SLAMF7, thereby making those cells more sensitive to anti-SLAMF7 Ab ADCC-mediated cytotoxicity.

To study the in vivo therapeutic efficacy of combined rhGal-9 and anti-SLAMF7 Ab treatment on MM tumor growth, two different mouse models are employed to help validate the dependency of NK cells to elicit ADCC-mediated inhibition tumor growth. 6-8-week old NK cell—NOD-SCID/IL-2Rγ−/− (NSG) mice are used, and NK cell+ B6.Cg-Prkdc$^{scid}$/SzJ (SCID) mice purchased from JAX Labs are used to assay rhGal-9/anti-SLAMF7 Ab efficacy on MM xenografts. Elotuzumab (Elo) anti-SLAMF7 Ab are purchased from Bristol-Myers Squibb, and rhGal-9 is purchased (R&D Systems) and used at in vivo doses. Mice, including equal numbers of males/females, are inoculated with human MM SLAMF7 hi KMS-12-BM, SLAMF7 hi IM-9, or control SLAMF7—RPMI-8226 cells at $1\times10^6$ into the lower right flank. Tumor size is monitored and measured every other day for 3-weeks. Once tumors reach ~200 mm³, mice are randomized into 8 mice/group and injected i.p. as follows:

1.) Gal-9 vehicle (q.d., 14 days)/Elo vehicle (3/week);
2.) Gal-9 vehicle (q.d., 14 days)/Elo (10 mg/kg) (3/week);
3.) 5 mg/kg Gal-9 (q.d., 14 days)/Elo vehicle (3/week); and
4.) 5 mg/kg Gal-9 (q.d., 14 days)/Elo (10 mg/kg) (3/week).

In control mice, peripheral blood is monitored for NK cell depletion by FACS staining with anti-CD45 and DX5 (BD Biosciences). Results provide mechanistic insights on how Gal-9 can bind to and activate SLAMF7 in human MM cells. These results further support Gal-9 as a novel therapeutic for treating MM. These data rationalize novel strategies with Gal-9 to boost the efficacy of promising anti-SLAMF7 Ab Elo therapy for the lethal, incurable MM disease.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

I claim:

1. A method for treating a B cell malignancy in a subject in need of such treatment, comprising A) administering to the subject a composition comprising a functional galectin molecule to increase the expression of signaling lymphocytic activation molecule F7 (SLAMF7) in B cells and/or multiple myeloma cells; and B) administering to the subject a composition comprising an anti-SLAMF7 antibody, the functional galectin molecule being galectin-9 protein or a nucleotide sequence encoding the galectin-9 protein.

2. The method of claim 1, the B cell malignancy being a B cell derived cancer.

3. The method of claim 1, the B cell malignancy being multiple myeloma.

4. The method of claim 1, the anti-SLAMF7 antibody being Elotuzumab.

5. The method of claim 1, each administration being independently selected from local, oral, nasal, topical, intratumoural, transdermal, intra-articular, intravenous, intraperitoneal, intradermal, subcutaneous, and intramuscular routes.

6. A method for treating multiple myeloma in a subject, comprising
A) administering to the subject a composition comprising
1) a nucleic acid sequence that encodes Gal-9 or a nucleic acid sequence that encodes a protein sharing at least 95% identity with Gal-9, 2) an amino acid sequence of Gal-9 or an amino acid sequence sharing at least 95% identity with Gal-9, 3) a vector comprising a nucleic acid sequence that encodes Gal-9 or a nucleic acid sequence that encodes a protein sharing at least 95% identity with Gal-9, 4) a cell that overexpresses a nucleic acid sequence of Gal-9 or a nucleic acid sequence that encodes a protein sharing at least 95% identity with Gal-9, and/or 5) a cell that overexpresses an amino acid sequence of Gal-9, to increase the expression of SLAMF7 in multiple myeloma cells; and
B) administering to the subject an anti-SLAMF7 antibody.

7. The method of claim 6, the anti-SLAMF7 antibody being Elotuzumab.

8. The method of claim 6, each administration being independently selected from local, oral, nasal, topical, intratumoural, transdermal, intra-articular, intravenous, intraperitoneal, intradermal, subcutaneous, and intramuscular routes.

9. A method for improving the sensitivity of multiple myeloma cells of a subject to an immunotherapy, the method comprising:

A) administering to the subject a composition comprising 1) a nucleic acid sequence that encodes Gal-9 or a nucleic acid sequence that encodes a protein sharing at least 95% identity with Gal-9, 2) an amino acid sequence of Gal-9 or an amino acid sequence sharing at least 95% identity with Gal-9, 3) a vector comprising a nucleic acid sequence that encodes Gal-9 or a nucleic acid sequence that encodes a protein sharing at least 95% identity with Gal-9, 4) a cell that overexpresses a nucleic acid sequence of Gal-9 or a nucleic acid sequence that encodes a protein sharing at least 95% identity with Gal-9, and/or 5) a cell that overexpresses an amino acid sequence of Gal-9, to increase the expression of SLAMF7 in multiple myeloma cells; and B) administering to the subject the immunotherapy.

10. The method of claim 9, the immunotherapy being an antibody therapy.

11. The method of claim 10, the antibody therapy comprising administering to the subject an anti-SLAMF7 antibody.

12. The method of claim 11, the anti-SLAMF7 antibody being Elotuzumab.

13. The method of claim 9, further comprising detecting SLAMF7 level before and/or after step A).

14. The method of claim 1, further comprising detecting the expression of SLAMF7 before and/or after administering the composition comprising the functional galectin molecule.

15. The method of claim 6, further comprising detecting the expression of SLAMF7 before and/or after step A).

16. The method of claim 1, further comprising detecting SLAMF7 level before and/or after step A).

17. The method of claim 1, wherein administering the composition increases the expression of SLAMF7 in B cells and multiple myeloma cells.

18. The method of claim 1, wherein administering the composition increases the expression of SLAMF7 in multiple myeloma cells.

19. The method of claim 1, wherein administering the composition increases the expression of SLAMF7 in B cells.

* * * * *